United States Patent
Wang et al.

(10) Patent No.: US 10,772,844 B2
(45) Date of Patent: Sep. 15, 2020

(54) HYBRID HYDROGEL AND METHOD OF FABRICATING THE SAME

(71) Applicant: National Tsing Hua University, Hsinchu (TW)

(72) Inventors: Tzu-Wei Wang, Hsinchu (TW); Wei-Hong Jian, Hsinchu (TW)

(73) Assignee: National Tsing Hua University, Hsinchu (TW)

(*) Notice: Subject to any disclaimer, the term of this patent is extended or adjusted under 35 U.S.C. 154(b) by 0 days.

(21) Appl. No.: 16/180,016

(22) Filed: Nov. 5, 2018

(65) Prior Publication Data

US 2020/0093752 A1 Mar. 26, 2020

(30) Foreign Application Priority Data

Sep. 20, 2018 (TW) .............................. 107133096 A

(51) Int. Cl.
| | |
|---|---|
| *A61K 9/51* | (2006.01) |
| *A61K 38/18* | (2006.01) |
| *A61K 38/19* | (2006.01) |
| *A61L 27/20* | (2006.01) |
| *A61L 27/26* | (2006.01) |
| *A61L 27/52* | (2006.01) |
| *A61L 27/58* | (2006.01) |
| *A61L 27/54* | (2006.01) |

(52) U.S. Cl.
CPC .......... *A61K 9/5161* (2013.01); *A61K 9/5192* (2013.01); *A61K 38/1825* (2013.01); *A61K 38/195* (2013.01); *A61L 27/20* (2013.01); *A61L 27/26* (2013.01); *A61L 27/52* (2013.01); *A61L 27/54* (2013.01); *A61L 27/58* (2013.01); *A61L 2300/414* (2013.01); *A61L 2300/426* (2013.01)

(58) Field of Classification Search
CPC .... A61K 38/195; A61K 47/36; A61K 9/5192; A61K 38/1825; A61L 27/54; A61L 27/58; A61L 27/50

See application file for complete search history.

(56) References Cited

U.S. PATENT DOCUMENTS

| | | | | |
|---|---|---|---|---|
| 5,762,918 A | * | 6/1998 | Thorpe ............... | A61K 47/61 424/78.17 |
| 7,291,598 B2 | * | 11/2007 | Sung ................... | A61K 9/5146 424/1.33 |
| 2007/0065415 A1 | | 3/2007 | Kleinsek et al. | |
| 2007/0248675 A1 | | 10/2007 | Tae et al. | |
| 2007/0280974 A1 | * | 12/2007 | Son ..................... | A61K 8/0208 424/401 |
| 2011/0123592 A1 | * | 5/2011 | Stevens .............. | A61L 27/227 424/423 |
| 2014/0342984 A1 | | 11/2014 | Matheny | |
| 2018/0355121 A1 | * | 12/2018 | Akbari ................ | A61K 9/5026 |

FOREIGN PATENT DOCUMENTS

WO     03099230     12/2003

OTHER PUBLICATIONS

Jian; Wei-Hong et al, "Glycosaminoglycan-based hybrid hydrogel encapsulated with polyelectrolyte complex nanoparticles for endogenous stem cell regulation in central nervous system regeneration," Biomaterials, vol. 174, Aug. 2018, pp. 17-30.

Lim TC, et al., "Chemotactic recruitment of adult neural progenitor cells into multifunctional hydrogels providing sustained SDF-1α release and compatible structural support." The FASEB Journal, vol. 27, No. 23, Mar. 2013, pp. 1023-1033.

"Office Action of Taiwan Counterpart Application," dated Jul. 26, 2019, p. 1-p. 11.

* cited by examiner

*Primary Examiner* — Mina Haghighatian
(74) *Attorney, Agent, or Firm* — JCIPRNET

(57) ABSTRACT

A hybrid hydrogel including a hydrogel material and a plurality of first hybrid nanoparticles is provided. The plurality of first hybrid nanoparticles are conjugated to the hydrogel material, wherein each of the first hybrid nanoparticles includes a first positive-charged polysaccharide and a first negative-charged polysaccharide. The first positive-charged polysaccharide is located at an inner core of the first hybrid nanoparticles. The first negative-charged polysaccharide is located at an outer shell of the first hybrid nanoparticles and carries a plurality of first growth factors. The first negative-charged polysaccharide and the first positive-charged polysaccharide are electrostatically attracted to form the first hybrid nanoparticles. A method of fabricating the hybrid hydrogel is also provided.

15 Claims, 23 Drawing Sheets

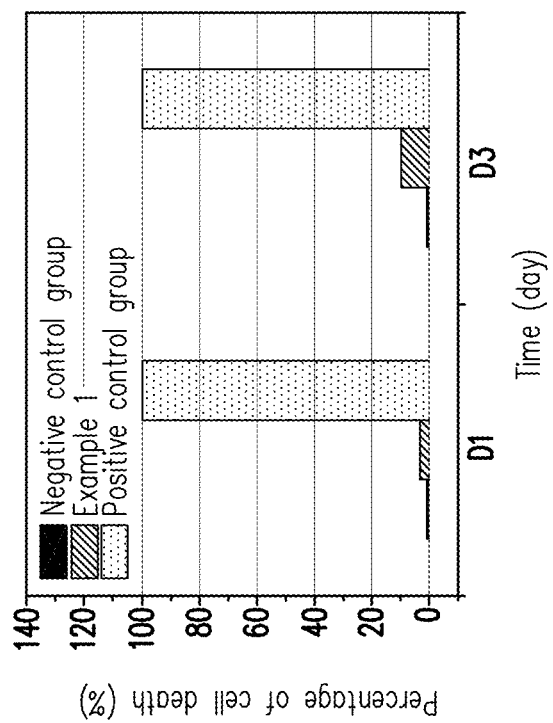
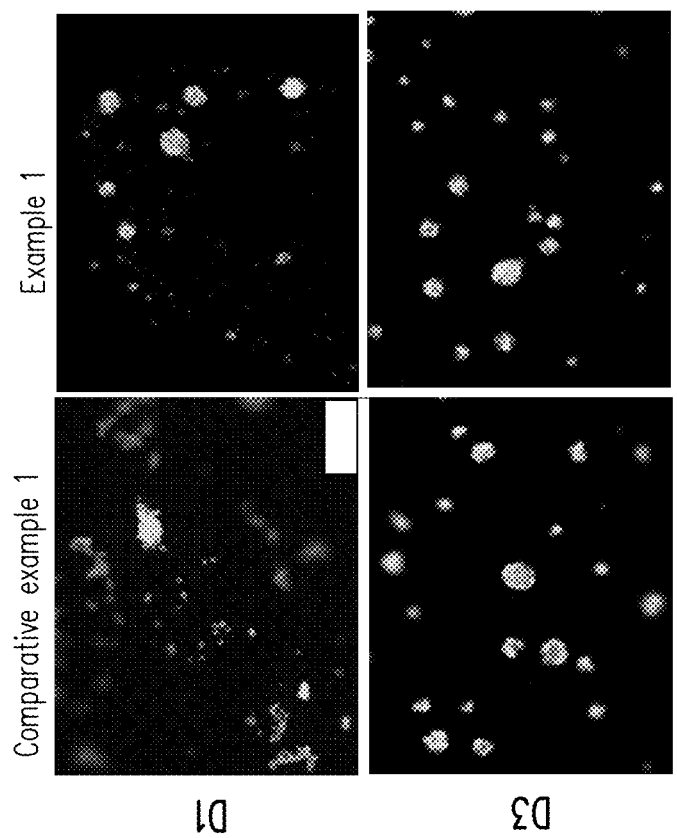
FIG. 7B
FIG. 7A

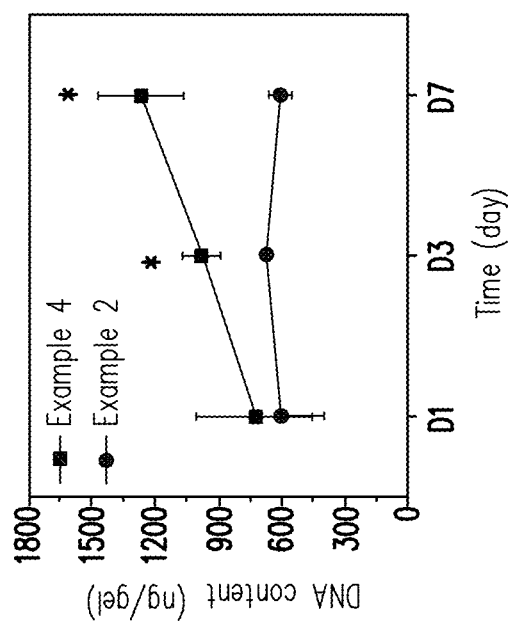
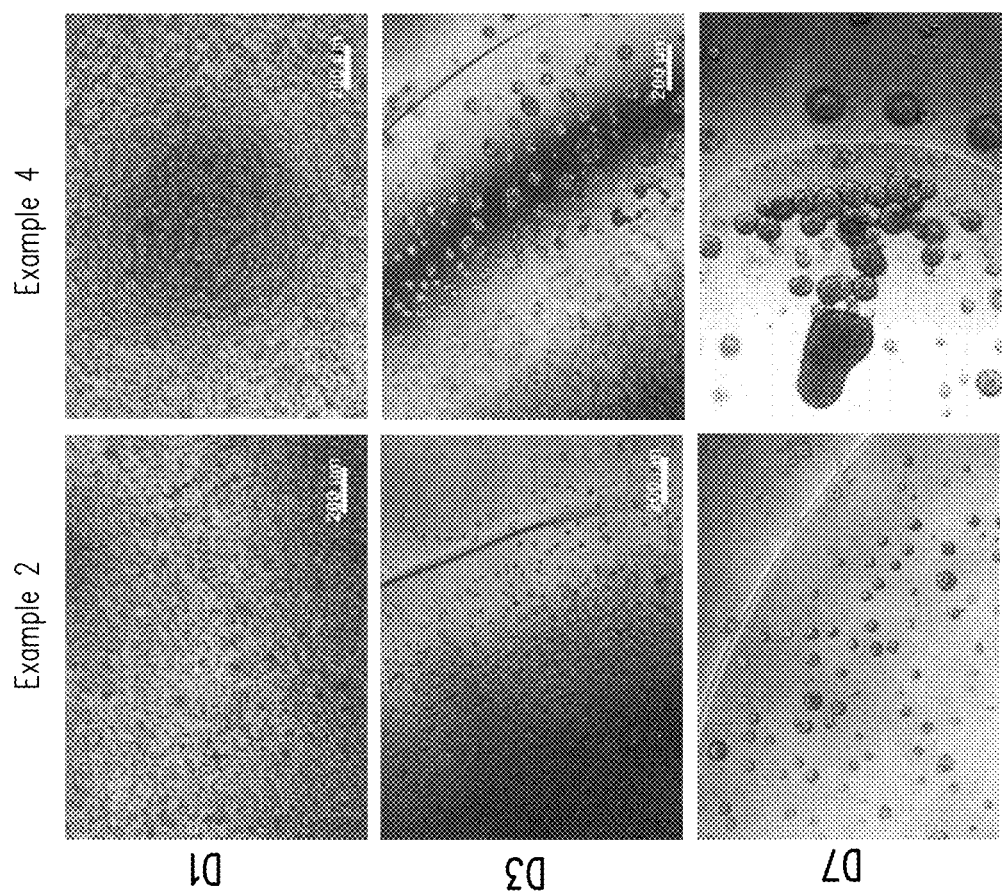
FIG. 10B
FIG. 10A

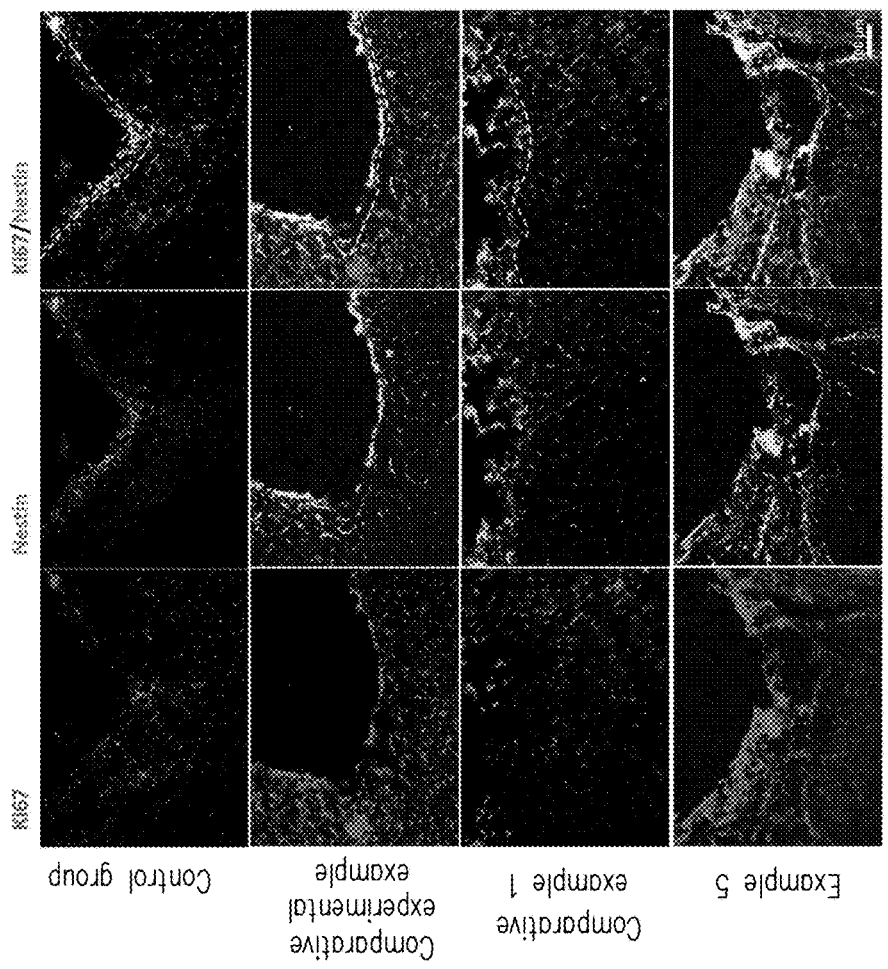
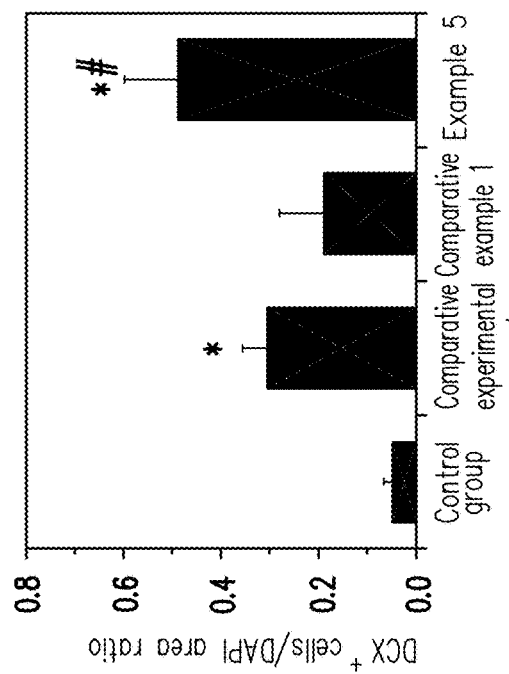
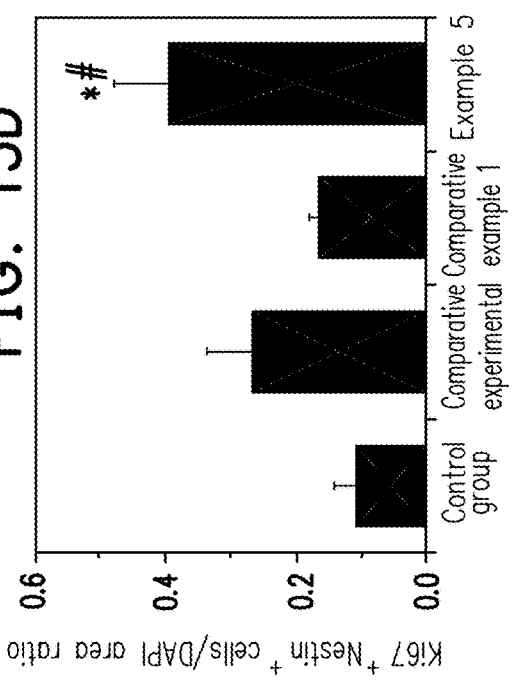
FIG. 13C
FIG. 13D
FIG. 13E

HYBRID HYDROGEL AND METHOD OF FABRICATING THE SAME

CROSS-REFERENCE TO RELATED APPLICATION

This application claims the priority benefit of Taiwan application serial no. 107133096, filed on Sep. 20, 2018. The entirety of the above-mentioned patent application is hereby incorporated by reference herein and made a part of this specification.

BACKGROUND OF THE INVENTION

Field of the Invention

The invention relates to a hydrogel and a method of fabricating the same, and more particularly, to a hybrid hydrogel and a method of fabricating the same.

Description of Related Art

Both traumatic and vascular brain damage usually cause damage to the nerve tissue at the initial lesion which leads to permanent neurological deficit. At present, there are still many areas for improvement in the treatment of brain damage. For example, in drug therapy, the thrombolytic agent (tPA) approved by the Food and Drug Administration (FDA) has the disadvantages of narrow therapeutic window and not actively promoting brain tissue regeneration. In cell therapy, in the treatment of dysfunctional cells or dead cells by replacing or repairing them with stem cell transplant, in addition to overcoming issues such as cell source and donor cell maturity, inflammatory microenvironment, structural support, trophic factors, and cell viability or engraftment rate are also conditions to be considered. Therefore, how to improve the treatment-expensive and complicated ex vivo process technique is one of the issues that those skilled in the art are currently trying to solve.

SUMMARY OF THE INVENTION

The invention provides a hybrid hydrogel that may be used for drug therapy or cell therapy, and a suitable combination of a hydrogel material and hybrid nanoparticles may be selected according to requirements to achieve a better treatment effect.

The hybrid hydrogel of the invention includes a hydrogel material and a plurality of first hybrid nanoparticles. The first hybrid nanoparticles are conjugated to the hydrogel material, wherein each of the first hybrid nanoparticles includes a first positive-charged polysaccharide and a first negative-charged polysaccharide. The first positive-charged polysaccharide is located at an inner core of the first hybrid nanoparticles. The first negative-charged polysaccharide is located at an outer shell of the first hybrid nanoparticles and carries a plurality of first growth factors. The first negative-charged polysaccharide and the first positive-charged polysaccharide are electrostatically attracted to form the first hybrid nanoparticles.

In an embodiment of the invention, the hybrid hydrogel further includes a plurality of second hybrid nanoparticles conjugated to the hydrogel material, wherein each of the second hybrid nanoparticles includes a second positive-charged polysaccharide and a second negative-charged polysaccharide. The second positive-charged polysaccharide is located at an inner core of the second hybrid nanoparticles. The second negative-charged polysaccharide is located at an outer shell of the second hybrid nanoparticles and carries a plurality of second growth factors. The second negative-charged polysaccharide and the second positive-charged polysaccharide are electrostatically attracted to form the second hybrid nanoparticles.

In an embodiment of the invention, the plurality of first hybrid nanoparticles and the plurality of second hybrid nanoparticles are conjugated to the hydrogel material by an enzyme-sensitive bond or a non-enzyme-sensitive bond.

In an embodiment of the invention, the plurality of first hybrid nanoparticles are conjugated to the hydrogel material by an enzyme-sensitive bond, and the plurality of second hybrid nanoparticles are conjugated to the hydrogel material by a non-enzyme-sensitive bond.

In an embodiment of the invention, the first negative-charged polysaccharide, and the second negative-charged polysaccharide include proteoglycan.

In an embodiment of the invention, the first positive-charged polysaccharide and the second positive-charged polysaccharide include chitosan.

In an embodiment of the invention, the first negative-charged polysaccharide and the second negative-charged polysaccharide include heparan sulfate, chondroitin sulfate, dermatan sulfate, keratin sulfate, or a combination thereof.

In an embodiment of the invention, the first growth factors and the second growth factors include basic fibroblast growth factors (bFGF), stromal cell-derived factor-1 alpha (SDF-1α), platelet-derived growth factors (PDGF), vascular endothelial growth factors (VEGF), hepatocyte growth factors (HGF), bone morphogenetic proteins (BMP), or a combination thereof.

In an embodiment of the invention, the first growth factors and the second growth factors are the same or different growth factors.

In an embodiment of the invention, the hydrogel material includes a biodegradable hydrogel material.

In an embodiment of the invention, the hydrogel material includes glycosaminoglycan, polysaccharide, protein, or a combination thereof.

In an embodiment of the invention, the hydrogel material includes hyaluronic acid, alginic acid, chitosan, collagen, or a combination thereof.

In an embodiment of the invention, particle sizes of the plurality of first hybrid nanoparticles and the plurality of second hybrid nanoparticles are between 100 nm and 500 nm.

In an embodiment of the invention, a molecular weight of the first positive-charged polysaccharide is smaller than a molecular weight of the first negative-charged polysaccharide, and a molecular weight of the second positive-charged polysaccharide is smaller than a molecular weight of the second negative-charged polysaccharide.

In an embodiment of the invention, a storage modulus of the hybrid hydrogel after gelation is between 100 Pa and 1000 Pa.

A method of fabricating the hybrid hydrogel of the invention includes the following steps. A hydrogel material is provided. A plurality of first hybrid nanoparticles conjugated to the hydrogel material are formed, wherein each of the first hybrid nanoparticles includes a first positive-charged polysaccharide and a first negative-charged polysaccharide. The first positive-charged polysaccharide is located at an inner core of the first hybrid nanoparticles. The first negative-charged polysaccharide is located at an outer shell of the first hybrid nanoparticles and carries a plurality of first growth factors. The first negative-charged polysaccharide and the first positive-charged polysaccharide are electrostatically attracted to form the first hybrid nanoparticles.

In an embodiment of the invention, the method of fabricating the hybrid hydrogel further includes the following step. A plurality of second hybrid nanoparticles conjugated to the hydrogel material are formed, wherein each of the second hybrid nanoparticles includes a second positive-charged polysaccharide and a second negative-charged polysaccharide. The second positive-charged polysaccharide is located at an inner core of the second hybrid nanoparticles. The second negative-charged polysaccharide is located at an outer shell of the second hybrid nanoparticles and carries a plurality of second growth factors. The second negative-charged polysaccharide and the second positive-charged polysaccharide are electrostatically attracted to form the second hybrid nanoparticles.

In an embodiment of the invention, the plurality of first hybrid nanoparticles and the plurality of second hybrid nanoparticles are conjugated to the hydrogel material by an enzyme-sensitive bond or a non-enzyme-sensitive bond.

In an embodiment of the invention, the step of forming the plurality of first hybrid nanoparticles includes modifying the first negative-charged polysaccharide, wherein the modified first negative-charged polysaccharide is conjugated to an enzyme-sensitive peptide or a non-enzyme-sensitive peptide.

In an embodiment of the invention, the first growth factors and the second growth factors are the same or different growth factors.

Based on the above, the hybrid hydrogel of the invention includes a hydrogel material and hybrid nanoparticles, and a suitable combination of hydrogel material and hybrid nanoparticles may be selected according to requirements to achieve a better treatment effect. In therapeutic applications of brain damage, the hydrogel material may mimic the microenvironment of brain tissue and achieve the effect of structural support. The negative-charged polysaccharide in the hybrid nanoparticles may protect and carry different growth factors, and the load efficiency of the growth factors is high. The peptides that are conjugated to the hydrogel material and the hybrid nanoparticles may regulate the release rate of the hybrid nanoparticles, thereby controlling the release of the growth factors carried by the hybrid nanoparticles to achieve better treatment effects.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 7A is a fluorescence analysis image for a cytotoxicity test of the hybrid hydrogels of example 1 and comparative example 1 of the invention.

FIG. 7B is a diagram of the cytotoxicity test analysis of the hybrid hydrogel of example 1 of the invention.

FIG. 10A is a microscopic observation image of a cell proliferation assay of the combinations of the hybrid hydrogel and Matrigel of example 2 and example 4 of the invention.

FIG. 10B is a diagram of the analysis of cell proliferation assay of the combinations of the hybrid hydrogel and Matrigel of example 2 and example 4 of the invention.

FIG. 13A to FIG. 13C are immunofluorescence staining images of brain tissue sections for treating brain damage in rats using the hybrid hydrogel of example 5, the hydrogel of comparative example 1, the hybrid nanoparticles of the comparative experimental example, and the control group of the invention.

FIG. 13D and FIG. 13E are diagrams of the result analysis for treating brain damage in rats using the hybrid hydrogel of example 5, the hydrogel of comparative example 1, the hybrid nanoparticles of the comparative experimental example, and the control group of the invention shown according to immunofluorescence staining images of brain tissue sections.

DESCRIPTION OF THE EMBODIMENTS

In the present specification, a range represented by "a numerical value to another numerical value" is a schematic representation for avoiding listing all of the numerical values in the range in the specification. Therefore, the recitation of a specific numerical range covers any numerical value in the numerical range and a smaller numerical range defined by any numerical value in the numerical range, as is the case with the any numerical value and the smaller numerical range stated explicitly in the specification.

In the following, embodiments are provided to further describe the invention, but the embodiments are only exemplary and are not intended to limit the scope of the invention.

[Hybrid Nanoparticles]

FIG. 1A to FIG. 1E are schematic structural views showing a fabrication flow of hybrid nanoparticles according to some embodiments of the invention.

Figure 1C:
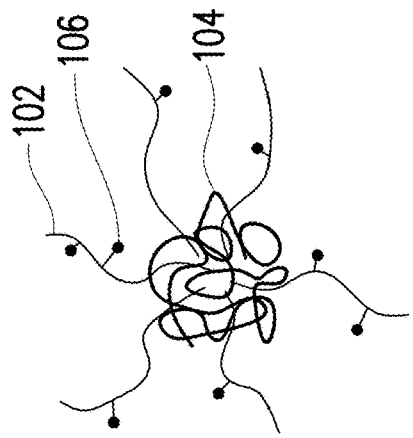
FIG. 1A to FIG. 1E are schematic structural views showing a fabrication flow of hybrid nanoparticles according to some embodiments of the invention.
Figure 1E:
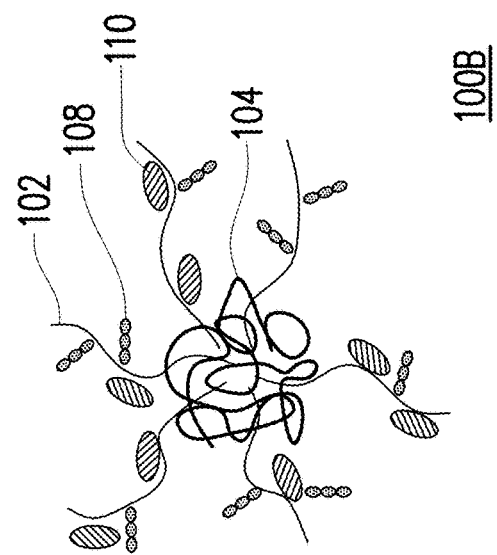
Figure 1B:
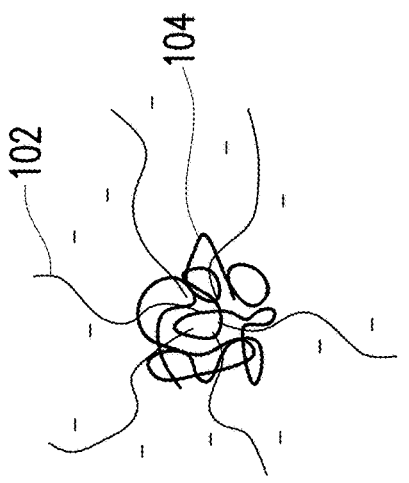
Figure 1D:
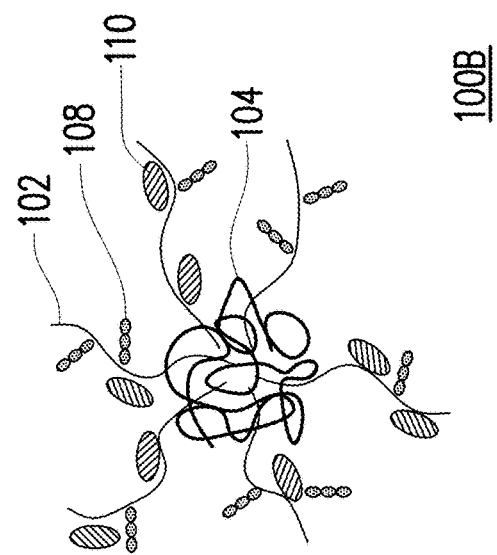
Figure 1A:
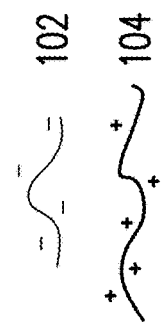

First, referring to FIG. 1A, a negative-charged polysaccharide 102 and a positive-charged polysaccharide 104 are provided. In some embodiments, the molecular weight of the positive-charged polysaccharide 104 is smaller than the molecular weight of the negative-charged polysaccharide 102. In other words, the molecular weight of the positive-charged polysaccharide 104 is about 30% to 50% of the molecular weight of the negative-charged polysaccharide 102. In a specific embodiment, the molecular weight of the positive-charged polysaccharide 104 is, for example, between 190,000 Daltons (Da) and 310,000 Da, and the molecular weight of the negative-charged polysaccharide 102 is, for example, between 600 kDa and 700 kDa. How-ever, the invention is not limited thereto. In some embodiments, the negative-charged polysaccharide 102 includes, for example, proteoglycan. In some embodiments, the negative-charged polysaccharide 102 includes, for example, heparan sulfate, chondroitin sulfate, dermatan sulfate, keratin sulfate, or a combination thereof, and the positive-charged polysaccharide 104 includes, for example, chitosan, but the invention is not limited thereto.

Next, referring to FIG. 1B, the negative-charged polysaccharide 102 and the positive-charged polysaccharide 104 are electrostatically attracted to form a nanocomposite. In some embodiments, the positive-charged polysaccharide 104 is located at the inner core of the nanocomposite, and the negative-charged polysaccharide 102 is located at the outer shell of the nanocomposite. It is worth mentioning that since the molecular weight of the positive-charged polysaccharide 104 is smaller than the molecular weight of the negative-charged polysaccharide 102, the negative-charged polysaccharide 102 located at the outer shell of the nanocomposite has space to be conjugated to a modified functional group in a subsequent step and carry growth factors by affinity.

Then, referring to both FIG. 1C and FIG. 1D, the negative-charged polysaccharide 102 is modified such that an enzyme-sensitive peptide 108 or a non-enzyme-sensitive peptide 108 is conjugated to the modified negative-charged polysaccharide 102 to form modified hybrid nanoparticles 100A. In some embodiments, the negative-charged polysaccharide 102 is modified first to have a suitable functional group, and then the enzyme-sensitive peptide 108 or the non-enzyme-sensitive peptide 108 is conjugated to the functional group. For example, the modified negative-charged polysaccharide 102 has a maleimide group 106, and then the enzyme-sensitive peptide 108 or the non-enzyme-sensitive peptide 108 is conjugated to the maleimide group 106, but the invention is not limited thereto. In a specific embodiment, 1-ethyl-3-3-dimethylaminopropyl carbodiimide hydrochloride (EDC) and N-hydroxysuccinimide (NHS) are added to be reacted with the negative-charged polysaccharide 102. The carboxyl group on the negative-charged polysaccharide 102 is activated by EDC cross-linking, and an NHS ester group conjugated to imine is formed. Then, N-(2-aminoethyl)maleimide trifluoroacetate salt is added to react, such that the modified negative-charged polysaccharide 102 has the maleimide group 106. Next, a thiol-maleimide click reaction is performed such that a thiol-terminated peptide is conjugated to the maleimide group 106 of the modified negative-charged polysaccharide 102. That is, the enzyme-sensitive peptide 108 or the non-enzyme-sensitive peptide 108 having a thiol-terminal group is conjugated to the maleimide group 106 of the modified negative-charged polysaccharide 102. In order to make the figure clear and concise, the maleimide group 106 is omitted in FIG. 1D.

In some embodiments, the enzyme refers to, for example, matrix metalloproteinase (MMP), but the invention is not limited thereto. Specifically, MMP is upregulated after brain damage and may degrade extracellular matrix (ECM) structural proteins during tissue remodeling, but the invention is not limited thereto. In some embodiments, the enzyme-sensitive peptide refers to, for example, an MMP-cleavable peptide, and the sequence thereof is, for example, GCDSGGRMSMPVSDGG. In some embodiments, the non-enzyme-sensitive peptide refers to, for example, an MMP-inactive peptide, and the sequence thereof is, for example, GCRDFGAIGQDGDRGG, but the invention is not limited thereto.

Then, referring to FIG. 1E, growth factors 110 are added such that the negative-charged polysaccharide 102 carries a plurality of growth factors 110 by affinity to form hybrid nanoparticles 100B. In some embodiments, the growth factors 110 include, for example, basic fibroblast growth factors (bFGF), stromal cell-derived factor-1 alpha (SDF-1α), platelet-derived growth factors (PDGF), vascular endothelial growth factors (VEGF), hepatocyte growth factors (HGF), bone morphogenetic proteins (BMP), or a combination thereof, but the invention is not limited thereto. It is worth mentioning that the negative-charged polysaccharide 102 not only has the function of carrying the growth factors 110, but also has the function of protecting the growth factors 110.

In some embodiments, the particle size of the hybrid nanoparticles 100B is, for example, between 100 nanometers and 500 nanometers. That is to say, when the hybrid nanoparticles 100B in an embodiment of the invention are applied to the repair of brain tissue, the particle size of the hybrid nanoparticles 100B may be controlled to a suitable range as needed to allow the hybrid nanoparticles 100B to be successfully encapsulated in the hydrogel to achieve an effective treatment effect, but the invention is not limited thereto. The particle size of the hybrid nanoparticles 100B of the invention may be adjusted to other suitable ranges according to different treatments and applications to achieve a better treatment effect.

[Hybrid Hydrogel]

Figure 2A:
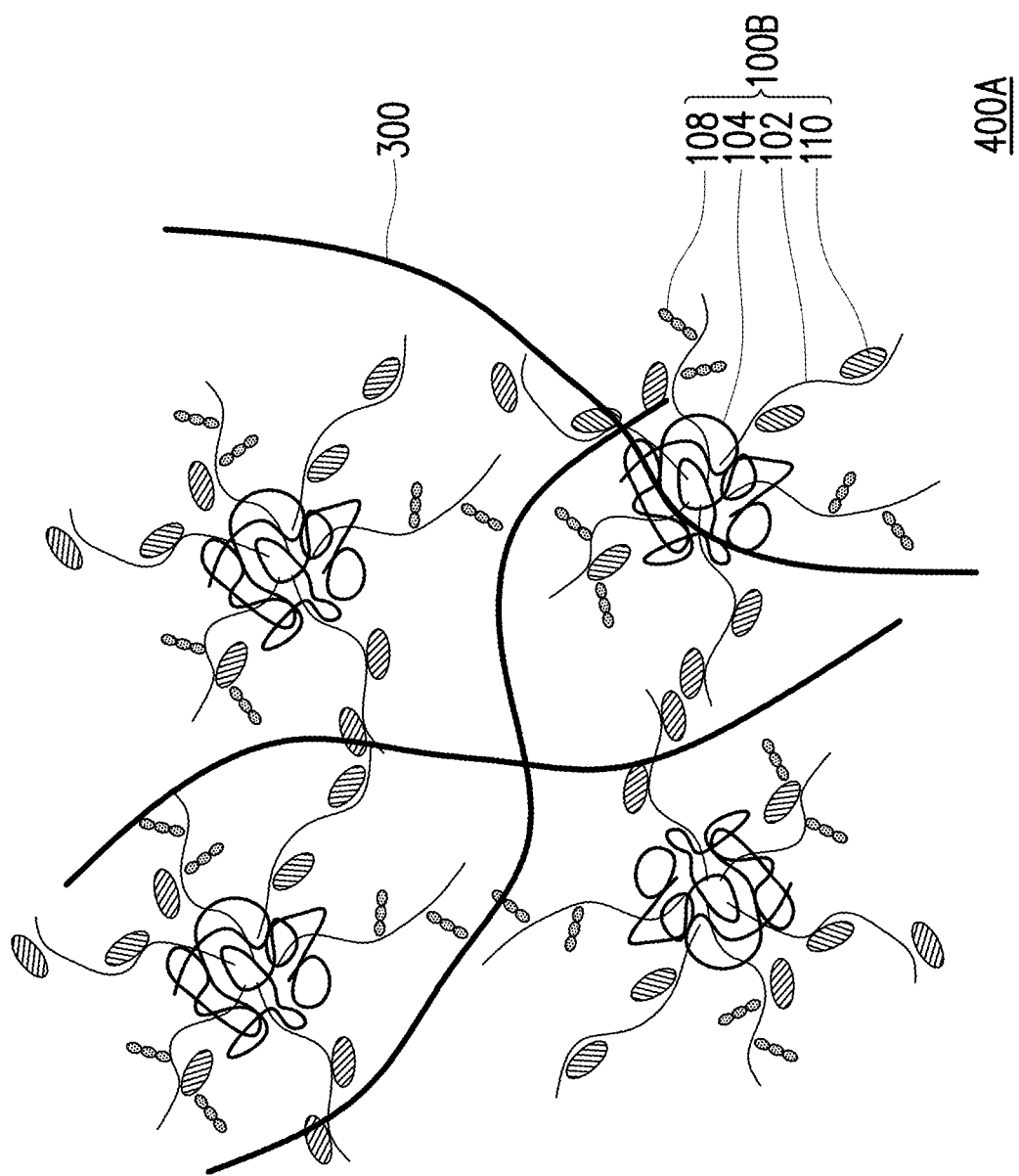
FIG. 2A and FIG. 2B are schematic structural views showing a hybrid hydrogel according to some embodiments the invention.
Figure 2B:
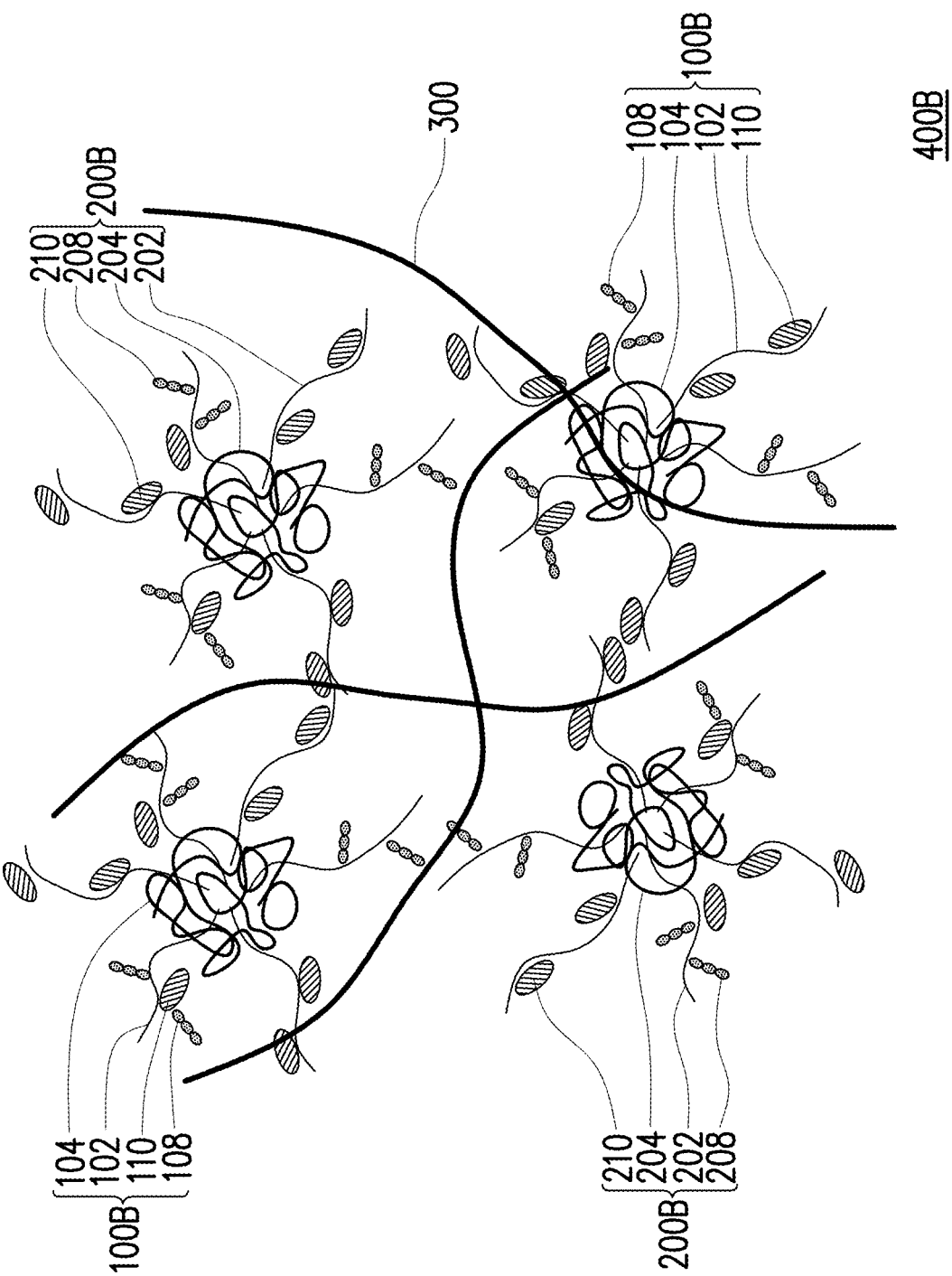

FIG. 2A and FIG. 2B are schematic structural views showing a hybrid hydrogel according to some embodiments the invention.

Referring to FIG. 2A, a hydrogel material 300 is provided. In some embodiments, the hydrogel material 300 includes, for example, a biodegradable hydrogel material. In some other embodiments, the hybrid material 300 includes, for example, glycosaminoglycan (GAG), polysaccharide, protein, or a combination thereof. For example, the GAG includes, for example, hyaluronic acid (hereinafter HA), and the polysaccharide includes, for example, alginic acid, chitosan, or a combination thereof. The protein includes, for example, collagen.

Next, a plurality of hybrid nanoparticles 100B are formed according to the method of fabricating the hybrid nanoparticles 100B above, and the hybrid nanoparticles 100B are conjugated to the hydrogel material 300, wherein the hybrid nanoparticles 100B are conjugated to the hydrogel material 300 by an enzyme-sensitive bond or a non-enzyme-sensitive bond. In some embodiments, the hydrogel material 300 and the hybrid nanoparticles 100B are modified first before conjugation to have a suitable functional group, and then the enzyme-sensitive peptide 108 or the non-enzyme-sensitive peptide 108 on the hybrid nanoparticles 100B is conjugated to the functional group. For example, the modified hydrogel material 300 has an aldehyde group, and then the enzyme-sensitive peptide 108 or the non-enzyme-sensitive peptide 108 on the hybrid nanoparticles 100B is conjugated to the aldehyde group, but the invention is not limited thereto. In a specific embodiment, sodium periodate (NaIO$_4$) is added to react with the hydrogel material 300 such that the modified hydrogel material 300 has an aldehyde group. Next, the modified hydrogel material 300 is reacted with the hybrid nanoparticles 100B such that the aldehyde group of the hydrogel material 300 and the amino group of the hybrid nanoparticles 100B (i.e., the amino group of the enzyme-sensitive peptide 108 or the non-enzyme-sensitive peptide 108 conjugated to the negative-charged polysaccharide 102) are reacted to form an imine bond. That is, in a formed hybrid hydrogel 400A, whether the hybrid nanoparticles 100B are conjugated to the hydrogel material 300 by an enzyme-sensitive bond or a non-enzyme-sensitive bond is decided according to whether the peptide conjugated to the negative-charged polysaccharide 102 of the hybrid nanoparticles 100B is the enzyme-sensitive peptide 108 or the non-enzyme-sensitive peptide 108. Specifically, when the peptide conjugated to the negative-charged polysaccharide 102 of the hybrid nanoparticles 100B is the enzyme-sensitive peptide 108, the hybrid nanoparticles 100B are conjugated to the hydrogel material 300 by an enzyme-sensitive bond. In other words, when the peptide conjugated to the negative-charged polysaccharide 102 of the hybrid nanoparticles 100B is the non-enzyme-sensitive peptide 108, the hybrid nanoparticles 100B are conjugated to the hydrogel material 300 by a non-enzyme-sensitive bond. It is worth mentioning that in the present embodiment (as shown in FIG. 2A), the hybrid nanoparticles 100B in the hybrid hydrogel 400A are the same, that is, the negative-charged polysaccharide 102, the positive-charged polysaccharide 104, the growth factors 110 carried by the hybrid nanoparticles 100B, and the (non-)enzyme-sensitive peptide 108 forming the hybrid nanoparticles 100B are the same, but the invention is not limited thereto.

Referring to FIG. 2B, the hybrid nanoparticles in the hybrid hydrogel 400B may be different. In other words, the hybrid hydrogel 400B may include different hybrid nanoparticles 100B and hybrid nanoparticles 200B. For example, the negative-charged polysaccharide 202 forming the hybrid nanoparticles 200B may be the same as or different from the negative-charged polysaccharide 102 forming the hybrid nanoparticles 100B, the positive-charged polysaccharide 204 forming the hybrid nanoparticles 200B may be the same as or different from the positive-charged polysaccharide 104 forming the hybrid nanoparticles 100B, the growth factors 210 carried by the hybrid nanoparticles 200B may be the same as or different from the growth factors 110 carried by the hybrid nanoparticles 100B, and a (non-)enzyme-sensitive peptide 208 conjugated to the hybrid nanoparticles 200B and the hydrogel material 300 may be the same as or different from the (non-)enzyme-sensitive peptide 108 conjugated to the hybrid nanoparticles 100B and the hydrogel material 300. In other words, the hybrid nanoparticles 200B may be adjusted to be the same as, partially the same as, or completely different from the hybrid nanoparticles 100B depending on the treatment or application requirements. Only the embodiments of two different hybrid nanoparticles are listed below, but the invention is not limited thereto, that is, the hybrid hydrogel may include two or more different hybrid nanoparticles.

In some embodiments, the growth factors 210 carried by the hybrid nanoparticles 200B are different from the growth factors 110 carried by the hybrid nanoparticles 100B. Specifically, different growth factors have different effects, and therefore the negative-charged polysaccharide may carry different growth factors to achieve different treatments or applications. In a specific embodiment, the growth factors 210 are, for example, SDF-1α, and the growth factors 110 are, for example, bFGF, but the invention is not limited thereto.

In other embodiments, the negative-charged polysaccharide 202 forming the hybrid nanoparticles 200B is different from the negative-charged polysaccharide 102 forming the hybrid nanoparticles 100B. Specifically, since different negative-charged polysaccharides have different affinities for growth factors, the suitable pairing may be adjusted by the different affinities between the negative-charged polysaccharide and the growth factors to achieve better loading efficiency. For example, heparan sulfate has a stronger affinity for SDF-1α, and chondroitin sulfate has a stronger affinity for bFGF. In a specific embodiment, the negative-charged polysaccharide 202 is, for example, heparan sulfate, and the growth factors 210 carried by the negative-charged polysaccharide 202 are, for example, SDF-1α. The negative-charged polysaccharide 102 is, for example, chondroitin sulfate, and the growth factors 110 carried by the negative-charged polysaccharide 102 are, for example, bFGF, but the invention is not limited thereto.

In other embodiments, the (non-)enzyme-sensitive peptide 208 conjugated to the hybrid nanoparticles 200B and the hydrogel material 300 is different from the (non-)enzyme-sensitive peptide 108 conjugated to the hybrid nanoparticles 100B and the hydrogel material 300. Specifically, an enzyme-sensitive peptide or a non-enzyme-sensitive peptide may be active or inactive for a particular enzyme, and therefore an enzyme-sensitive peptide or a non-enzyme-sensitive peptide may be selected to achieve different treatments or applications. For example, the peptide 208 conjugated to the hybrid nanoparticles 200B and the hydrogel material 300 is the enzyme-sensitive peptide 208, and the peptide 108 conjugated to the hybrid nanoparticles 100B and the hydrogel material 300 is the non-enzyme-sensitive peptide 108. In a specific embodiment, such as in the treatment of brain damage, the growth factors 210 carried by the negative-charged polysaccharide 202 are, for example, SDF-1α, and the peptide 208 conjugated to the hybrid nanoparticles 200B and the hydrogel material 300 is, for example, the enzyme-sensitive peptide 208. Since matrix metalloproteinase (MMP) is upregulated after brain damage, MMP may cleave the enzyme-sensitive peptide 208 such that the hybrid nanoparticles 200B may be detached from the hydrogel material 300, releasing SDF-1α to the brain tissue, thereby promoting nearby endogenous cells (for example, neural stem cells (NSC)) to migrate to the damaged portion. On the other hand, the growth factors 110 carried by the negative-charged polysaccharide 102 are, for example, bFGF, and the peptide 108 conjugated to the hybrid nanoparticles 100B and the hydrogel material 300 is, for example, the non-enzyme-sensitive peptide 108. Since MMP is not active against the non-enzyme-sensitive peptide 108, the hybrid nanoparticles 100B are slower to be detached from the hydrogel material 300, and therefore endogenous stem cells may be proliferated when the endogenous cells are migrated to the damaged portion, thereby achieving the object of effectively repairing brain damage.

It is worth mentioning that after the hybrid hydrogel 400A or the hybrid hydrogel 400B is formed, the hybrid hydrogel 400A or the hybrid hydrogel 400B may be in the form of a gel by a gelation process. Specifically, the hybrid hydrogel 400A or the hybrid hydrogel 400B formed according to the above embodiments is in the form of a solution, and the hybrid hydrogel 400A or the hybrid hydrogel 400B may be coagulated through ring-opening process and by the addition of a crosslinking agent. For example, the crosslinking agent includes, for example, adipic acid dihydrazide (ADH), carbodiimide, glutaraldehyde, or a combination thereof, but the invention is not limited thereto. The hardness, gelation time, etc. of the hybrid hydrogel 400A or the hybrid hydrogel 400B after gelation may all be adjusted to the desired hardness by controlling the oxidation degree and the type and amount, etc. of the crosslinking agent as needed. For example, in treatment applications of brain damage, to form a biomimetic brain tissue matrix, the hardness of the hybrid hydrogel 400A or the hybrid hydrogel 400B may be adjusted to a hardness close to that of the brain tissue matrix. In some embodiments, the storage modulus of the hybrid hydrogel after gelation is, for example, between 100 Pa and 1000 Pa. In some other embodiments, the storage modulus of the hybrid hydrogel after gelation is, for example, between 100 Pa and 400 Pa, but the invention is not limited thereto. That is, the hybrid hydrogel 400A or the hybrid hydrogel 400B after gelation may have a stromal support effect.

[Experiments]

The invention is more specifically described in the following with reference to experimental examples. Although the following experiments are described, the materials used and the amount and ratio thereof, as well as handling details and handling process . . . etc., may be suitably modified without exceeding the scope of the invention. Accordingly, restrictive interpretation should not be made to the invention based on the experiments described below.

Experiment 1

In the following, the characteristics of the hybrid nanoparticles of the invention are described in detail with reference to FIG. 3A to FIG. 3C and Table 1.

Experimental Example 1

Chondroitin sulfate sodium salt (hereinafter referred to as CS) was dissolved in 6 mL of deionized water, and 0.1 N hydrochloric acid was added to adjust the pH of the chondroitin sulfate solution to 4.7. Next, EDC and NHS were added to the chondroitin sulfate solution and stirred at room temperature for 15 minutes, and the carboxyl group on the chondroitin sulfate was activated by EDC crosslinking, and an NHS ester group conjugated to the imine was formed. Then, N-(2-aminoethyl)maleimide trifluoroacetate salt was added, and the reaction mixture was stirred at room temperature for 6 hours such that a primary amine was directly conjugated to the activated carboxyl group by an amide bond. Then, the resulting solution was dialyzed for 24 hours under gentle shaking in deionized water to remove excess coupling agent and reaction by-products. Lastly, the resulting polymer solution was lyophilized and stored at −10° C. to obtain chondroitin sulfate having a maleimide group (hereinafter referred to as CS-mal).

Next, 1.2 mg/mL of CS-mal and 0.6 mg/mL of chitosan (hereinafter referred to as Chi) were respectively dissolved in 0.1 M acetic acid solution, and 0.22 μm of a mixed cellulose ester (MCE) syringe filter was used for filtration. Next, the Chi solution was rapidly and all at once added to the stirring CS-mal solution at a volume ratio of 1:6 (Chi:CS-mal), and the mixture was vigorously stirred for 3 hours. Then, the resulting CS-mal/Chi nanocomposite was dialyzed in deionized water for 24 hours to remove the uncomplexed polymer.

Next, the CS-mal/Chi nanocomposite solution was mixed with a custom MMP-inactive peptide solution at a molar ratio of 1:1 (maleimide group:thiol group) at 4° C. for 4 hours, and the pH of the mixed solution was adjusted to a range of 6.5 to 7.5 to avoid side reactions to obtain MMP-inactive peptide modified chondroitin sulfate PCN (hereinafter referred to as mCSPCN) of experimental example 1.

Experimental Example 2

The hybrid nanoparticles of experimental example 2 were prepared according to a preparation procedure similar to experimental example 1, except that in experimental example 2, CS was replaced with heparan sulfate sodium salt (hereinafter referred to as HS). Therefore, HS having a maleimide group (hereinafter referred to as HS-mal) was obtained first, and then mixed with the Chi solution for subsequent steps. Further, in experimental example 2, the concentration of the Chi solution was adjusted to 0.3 mg/mL, and the MMP-inactive peptide solution was replaced with an MMP-cleavable peptide solution. Therefore, the hybrid nanoparticles obtained in experimental example 2 were MMP-cleavable peptide modified heparan sulfate PCN (hereinafter referred to as mHSPCN).

Experimental Example 3

The hybrid nanoparticles of experimental example 3 were prepared according to a preparation procedure similar to experimental example 1, except that in experimental example 3, the hybrid nanoparticles mCSPCN solution obtained in experimental example 1 was mixed with a bFGF solution in deionized water at a weight ratio of 100 ng/mg (bFGF/mCSPCN). Then, the bFGF-loaded hybrid nanoparticle mCSPCN solution was mixed with a sucrose solution (20% w/v) used as a refrigerant, and lastly, the mixture was lyophilized and stored at 4° C. Thus, the hybrid nanoparticles mCSPCN (bFGF-loaded) of experimental example 3 was obtained.

Experimental Example 4

The hybrid nanoparticles of experimental example 4 were prepared according to a preparation procedure similar to experimental example 3, except that in experimental example 4, the hybrid nanoparticle mCSPCN solution was replaced with the hybrid nanoparticle mHSPCN solution obtained in experimental example 2, and the bFGF solution was replaced with SDF-1α. Therefore, the hybrid nanoparticles mHSPCN (SDF-1α-loaded) of experimental example 4 were obtained.

Experimental Example 5

The hybrid nanoparticles of experimental example 5 were prepared according to a preparation procedure similar to experimental example 4, except that in experimental example 5, the MMP-cleavable peptide solution was replaced with an MMP-inactive peptide solution. Therefore, the hybrid nanoparticles obtained in experimental example 5 were MMP-inactive peptide-modified heparan sulfate PCN (hereinafter referred to as non-mHSPCN) (SDF-1α-loaded).

Comparative Experimental Example

The hybrid nanoparticles of comparative experimental example were prepared according to a preparation procedure similar to experimental example 3, except that in the comparison experimental example, the CS was not modified, that is, the hybrid nanoparticles were not conjugated to a maleimide group, and were not conjugated to the MMP-inactive peptide or the MMP-cleavable peptide, that is, in the comparative experimental example, the CS solution was directly mixed with the Chi solution, and then mixed with the bFGF solution. Therefore, the hybrid nanoparticles CSPCN (bFGF-loaded) of the comparative experimental example were obtained.

Figure 3B:
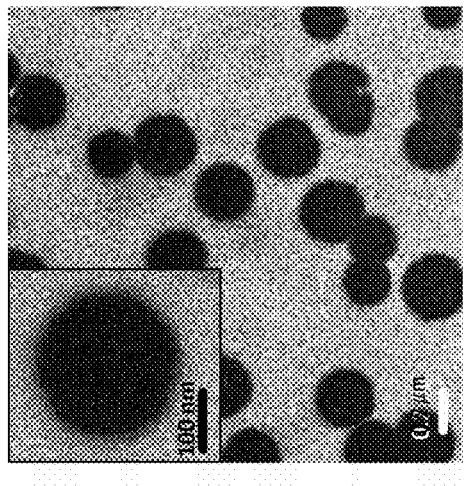
FIG. 3A and FIG. 3B are transmission electron microscope (TEM) images of the hybrid nanoparticles of experimental example 1 and experimental example 2 of the invention.
Figure 3A:
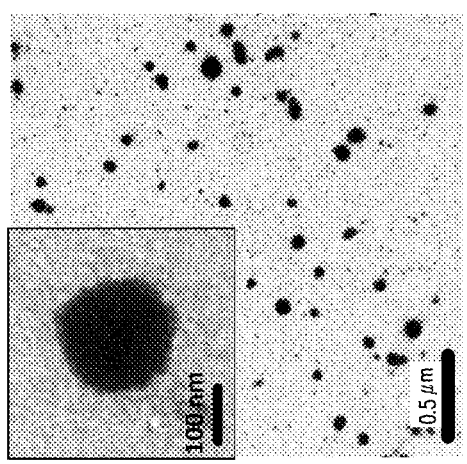
Figure 3C:
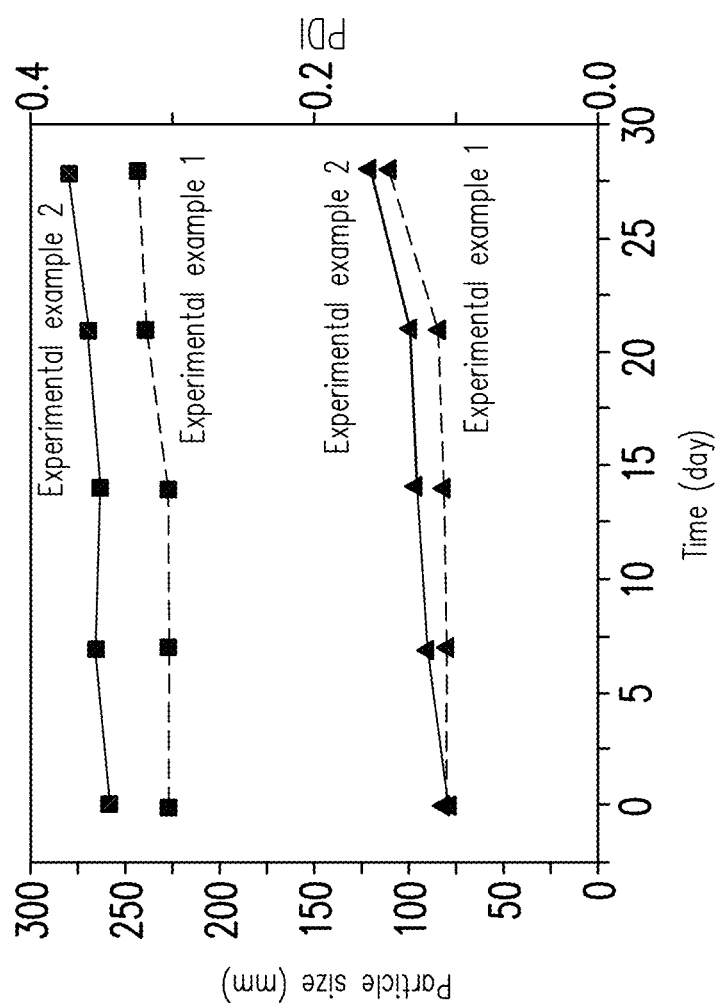
FIG. 3C is a particle size analysis diagram and a polymer dispersity index (PDI) analysis diagram of the hybrid nanoparticles of experimental example 1 and experimental example 2 of the invention.

FIG. 3A and FIG. 3B are transmission electron microscope (TEM) images of the hybrid nanoparticles of experimental example 1 and experimental example 2 of the invention. FIG. 3C is a particle size analysis diagram and a polymer dispersity index (PDI) analysis diagram of the hybrid nanoparticles of experimental example 1 and experimental example 2 of the invention. The morphology of the hybrid nanoparticles was observed by a TEM. The hydrodynamic size and ζ-potential of the hybrid nanoparticles were measured by a Malvern zeta-sizer. The growth factor loading efficiency was measured by an enzyme-linked immunosorbent assay (ELISA) kit. The results of particle size, polymer dispersity index, ζ-potential, particle yield, and growth factor loading efficiency of the hybrid nanoparticles of experimental example 1 to experimental example 4 are shown in Table 1 below.

TABLE 1

| | Particle size (nm) | Polymer dispersity index | ζ-potential (mV) | Particle yield (%) | Growth factor loading efficiency (%) |
|---|---|---|---|---|---|
| Experimental example 1 | 224.7 ± 4.0 | 0.134 ± 0.029 | −37.3 ± 2.3 | 36.1 | — |
| Experimental example 2 | 308.7 ± 28.7 | 0.216 ± 0.055 | −29.4 ± 8.2 | 24.7 | — |
| Experimental example 3 | 240.2 ± 22.5 | 0.131 ± 0.093 | −20.6 ± 9.7 | — | 53.7 ± 5.9 |
| Experimental example 4 | 287.4 ± 17.3 | 0.273 ± 0.019 | −25.8 ± 8.0 | — | 40.0 ± 2.3 |

As may be seen from the contents of FIG. 3A and FIG. 3B and Table 1, the hybrid nanoparticles of experimental example 1 to experimental example 4 are all negatively charged and may maintain a spherical shape, and the colloidal stability of the hybrid nanoparticles may be maintained for about one month. In addition, when hybrid nanoparticles carry growth factors, the particle size of the hybrid nanoparticles was not changed significantly, and the loading efficiency of the growth factors may reach 40% to 55%, thus reducing protein loss and maintaining the biological function thereof.

Experiment 2

Hereinafter, the characteristics of the hybrid hydrogel of the invention are described in detail with reference to FIG. 4A to FIG. 7B.

Example 1

First, HA was mixed with sodium periodate (NaIO$_4$) at a molar ratio of 1:1 (HA:IO$_4$) in the dark and at room temperature for 24 hours, then 1 mL of ethylene glycol was added to stop the reaction. Subsequently, the mixture was dialyzed in deionized water for 3 days and lyophilized to obtain aldehyde-functionalized HA (hereinafter referred to as HA-ALD).

Next, the hybrid nanoparticles mCSPCN obtained in experimental example 1 were dissolved in phosphate buffered saline (PBS) and mixed with 6 wt % HA-ALD powder at room temperature for 1 hour to form a composite mCSPCN-HA. In addition, ADH (8 wt %) was dissolved in PBS. Then, the composite mCSPCN-HA solution and the ADH solution were mixed by pipetting at the same volume, and a gelation reaction occurred in a few seconds to obtain the hybrid hydrogel mCSPCN-HA of example 1.

Example 2

The hybrid hydrogel of example 2 was prepared according to a preparation procedure similar to that of example 1, except that in example 2, the hybrid nanoparticle mCSPCN solution was replaced with the hybrid nanoparticle mHSPCN solution obtained in experimental example 2. Therefore, hybrid hydrogel mHSPCN-HA of example 2 was obtained.

Example 3

The hybrid hydrogel of example 3 was prepared according to a preparation procedure similar to that of example 1, except that in example 3, the hybrid nanoparticle mCSPCN solution was replaced with the hybrid nanoparticle mCSPCN (bFGF-loaded) solution obtained in experimental example 3. Therefore, hybrid hydrogel mCSPCN-HA (bFGF-loaded) of example 3 was obtained.

Example 4

The hybrid hydrogel of example 4 was prepared according to a preparation procedure similar to that of example 1, except that in example 4, the hybrid nanoparticle mCSPCN solution was replaced with the hybrid nanoparticle mHSPCN (SDF-1α-loaded) solution obtained in experimental example 4. Therefore, hybrid hydrogel mHSPCN-HA (SDF-1α-loaded) of example 4 was obtained.

Example 5

The hybrid hydrogel of example 5 was prepared according to a preparation procedure similar to that of example 1, except that in example 5, the hybrid nanoparticle mCSPCN solution was replaced with the hybrid nanoparticle mCSPCN (bFGF-loaded) solution obtained in experimental example 3 and the hybrid nanoparticle mHSPCN (SDF-1α-loaded) solution obtained in experimental example 4. Therefore, hybrid hydrogel mCS/HSPCN-HA (bFGF/SDF-1α-loaded) of example 5 was obtained.

Example 6

The hybrid hydrogel of example 6 was prepared according to a preparation procedure similar to that of example 1, except that in example 6, the hybrid nanoparticle mCSPCN solution was replaced with the hybrid nanoparticle non-mHSPCN (SDF-1α-loaded) solution obtained in experimental example 5. Therefore, hybrid hydrogel non-mHSPCN-HA (SDF-1α-loaded) of example 6 was obtained.

Comparative Example 1

The hybrid hydrogel of comparative example 1 was prepared according to a preparation procedure similar to that of example 1, except that in comparative example 1, HA was not modified, and the hybrid nanoparticles and growth factors were not added, that is, unmodified HA was directly reacted with ADH for gelation to obtain hydrogel HA of comparative example 1.

Comparative Example 2

The hybrid hydrogel of comparative example 2 was prepared according to a preparation procedure similar to that of example 1, except that in comparative example 2, the hybrid nanoparticle mCSPCN solution was replaced with the hybrid nanoparticle CSPCN (but not bFGF-loaded) solution obtained in the comparative experimental example. That is, the CS solution was directly mixed with the Chi solution, but was not mixed with the bFGF solution. Thus, the hybrid hydrogel CSPCN-HA of comparative example 2 was obtained. It should be noted that the hybrid nanoparticles CSPCN in the obtained hybrid hydrogel CSPCN-HA were not bonded and conjugated to HA, but only doped and mixed.

Figure 4B:
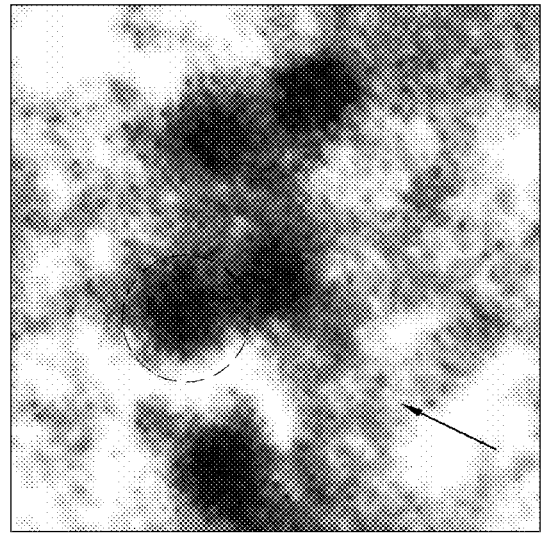
FIG. 4B is a partial enlarged view of FIG. 4A.
Figure 4A:
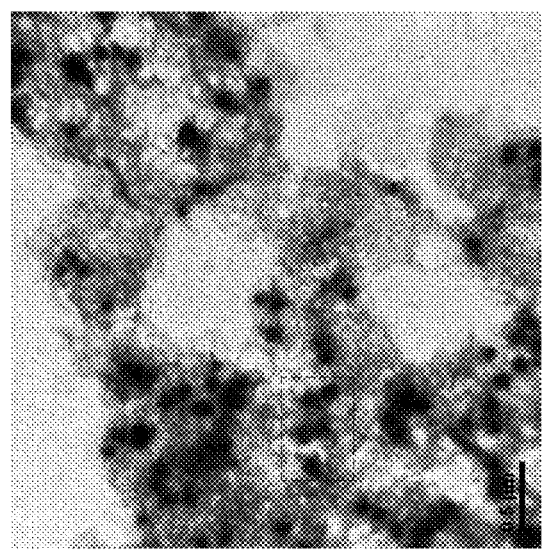
FIG. 4A is a TEM image of the hybrid hydrogel of example 1 of the invention.

FIG. 4A is a TEM image of the hybrid hydrogel of example 1 of the invention. FIG. 4B is a partial enlarged view of FIG. 4A. In FIG. 4B, the dotted circle represents the hybrid nanoparticles mCSPCN, and the arrow indicates the HA nanofibrous structure. It may be known from FIG. 4A and FIG. 4B that the hybrid hydrogel of example 1 shows that the hybrid nanoparticles mCSPCN were evenly distributed in the entangled HA nanofiber structure.

Figure 5A:
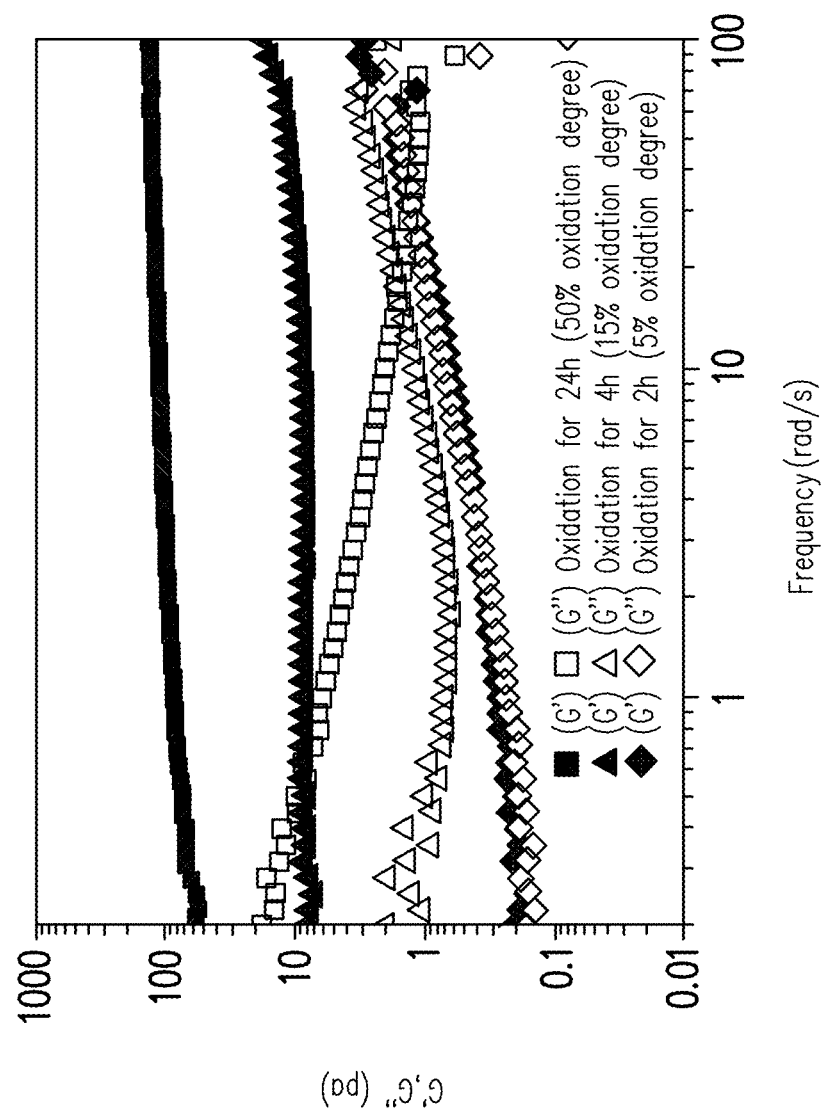
FIG. 5A is an analysis diagram of the mechanical properties of the hydrogel of comparative example 1 of the invention.
Figure 5B:
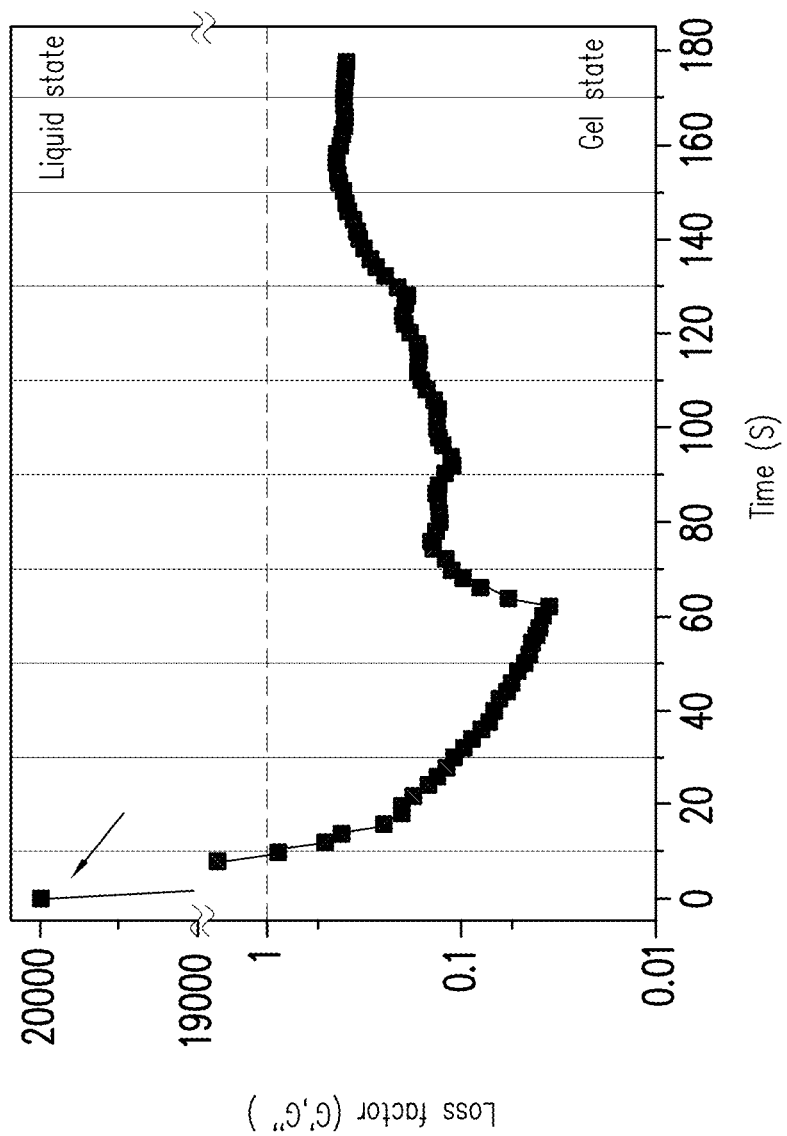
FIG. 5B is a diagram of time-dependent oscillatory shear rheology of the hybrid hydrogel of example 1 of the invention.
Figure 5C:
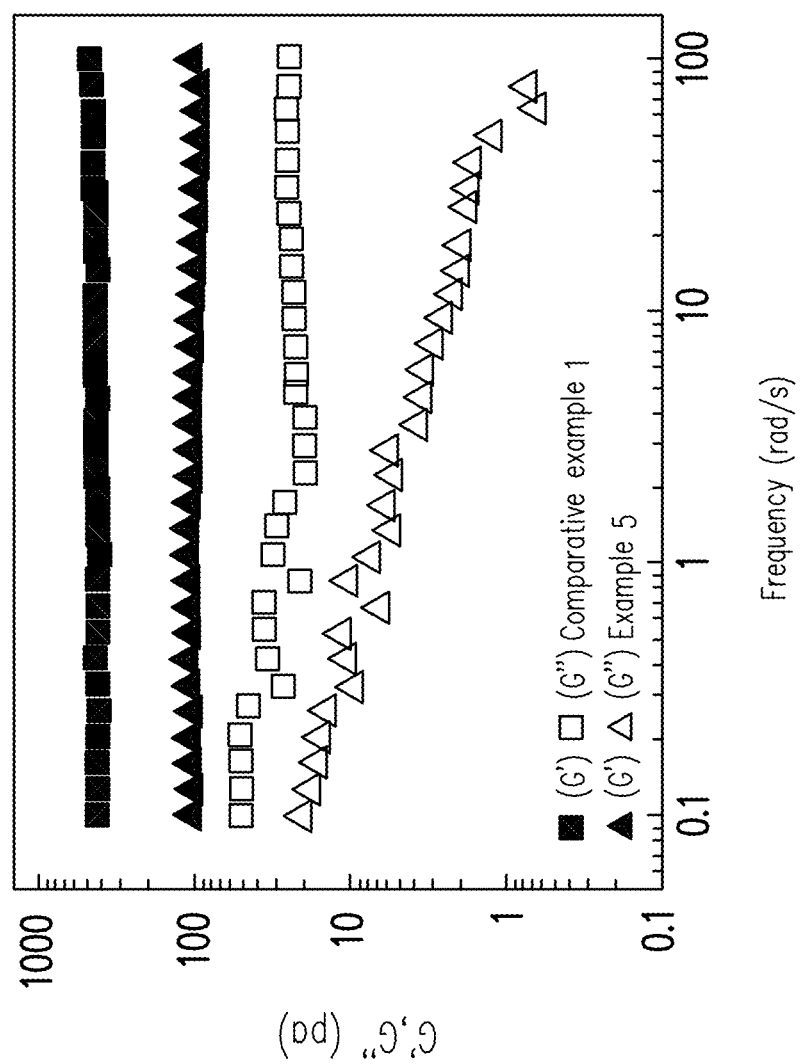
FIG. 5C is a diagram of frequency-dependent oscillatory shear rheology of the hybrid hydrogels of example 1 and comparative example 1 of the invention.

FIG. 5A is an analysis diagram of the mechanical properties of the hydrogel of comparative example 1 of the invention. FIG. 5B is a diagram of time-dependent oscillatory shear rheology of the hybrid hydrogel of example 1 of the invention. FIG. 5C is a diagram of frequency-dependent oscillatory shear rheology of the hybrid hydrogels of example 1 and comparative example 1 of the invention. The rheological property of the (hybrid) hydrogel was measured by a rheometer. The dynamic oscillation strain amplitude scan measurement was performed under the conditions of 25° C. and a frequency of 6.8 rad/s. The dynamic oscillation frequency scan measurement was performed under the condition of a strain amplitude of 50%.

In FIG. 5B, the arrow indicates the addition of ADH. As may be seen from FIG. 5A to FIG. 5B, by crosslinking HA-ALD having different oxidation degrees (50%, 15%, and 5%), the resulting hybrid hydrogel showed a different storage modulus, and the in situ gelation time of the hybrid hydrogel was within 10 seconds (loss factor<1). That is, the rheological properties of the hybrid hydrogel are affected by crosslink density and aldehyde-hydrazine condensation. In the present embodiment, in order to simulate the mechanical properties of brain tissue to achieve suitable hydrogel conjugation and prevent mechanical mismatch, subsequent hybrid hydrogel experiments adopted 50% oxidation degree conditions. In addition, as may be seen from FIG. 5C, the storage modulus (about 100 Pa) of the hybrid hydrogel of example 1 is slightly different from the storage modulus (about 400 Pa) of the hybrid hydrogel of comparative example 1. This is because the peptide conjugated to the hybrid hydrogel formed by the addition of the hybrid nanoparticles mCSPCN exposed the primary amine, thus consuming a portion of the aldehyde group of HA-ALD and resulting in a slight decrease in the crosslink density of the hybrid hydrogel.

Figure 6A:
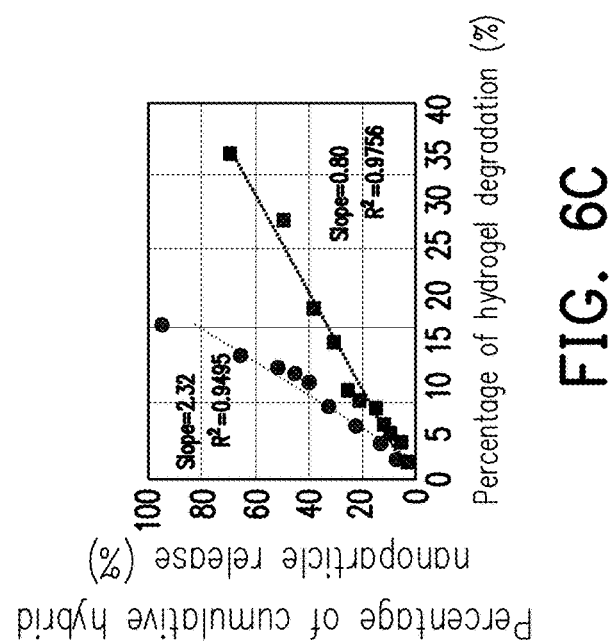
FIG. 6A to FIG. 6C are respectively a hydrogel degradation analysis diagram, a hybrid nanoparticle release analysis diagram, and a curve diagram of hydrogel degradation and hybrid nanoparticle release of the hybrid hydrogels of example 1 and comparative example 2 of the invention.
Figure 6B:
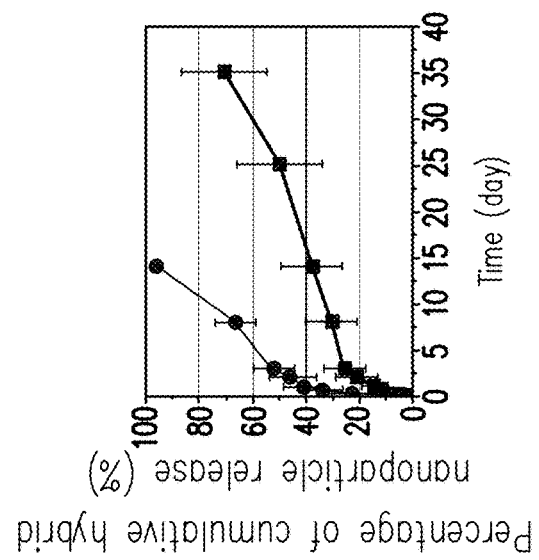
Figure 6C:
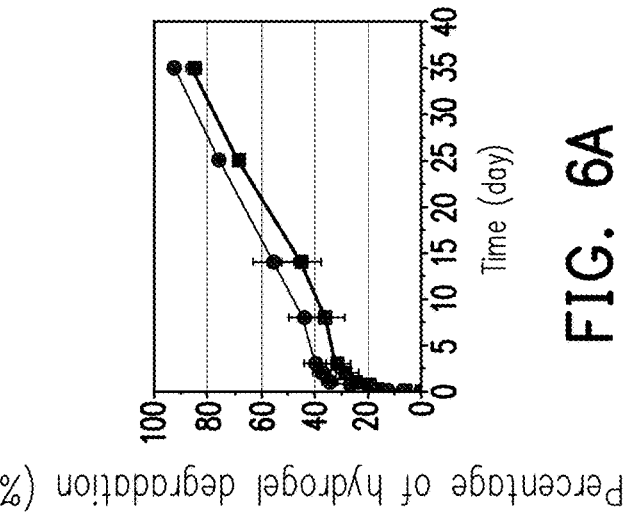

FIG. 6A to FIG. 6C are respectively a hydrogel degradation analysis diagram, a hybrid nanoparticle release analysis diagram, and a curve diagram of hydrogel degradation and hybrid nanoparticle release of the hybrid hydrogels of example 1 and comparative example 2 of the invention.

[Hydrogel Degradation Test]

40 μL of a hybrid hydrogel solution was placed in a cylindrical model for 30 minutes to form the hybrid hydrogel solution into a gel. Next, the cylindrical hybrid hydrogel was transferred to a 96-well plate, 100 μL of PBS was added to each well, and the supernatant was completely removed and replaced with fresh PBS at a fixed time (1, 3, 6, 9, 24, 48, 72, 168, 336, 600, and 840 hours) by a syringe. The glycosaminoglycan in the collected supernatant was measured using a cetyltrimethylammnonium bromide turbidimetric method (CTM).

[Hybrid Nanoparticles Release Test]

Before the hydrogel was coagulated, chitosan was first labeled with fluorescein isothiocyanate (FITC). Next, the hybrid hydrogel was cultured in PBS (37° C.), and the supernatant was completely removed and replaced with fresh PBS at a fixed time by a syringe. The FITC-labeled hybrid nanoparticles were measured using a VICTOR X3 microplate analyzer. In addition, to test the release regulation of MMP for the hybrid nanoparticles, 20 U/mL and 200 U/mL of a type-IV collagen enzyme were added in the PBS as a release buffer.

[Growth Factor Release Test]

40 μL of the hybrid hydrogel was incubated in 50 μL of the release buffer (PBS w/0.05% Tween 20, 1% BSA) (37° C.), and the supernatant was collected and 50 L of fresh release buffer was supplemented on days 1, 2, 3, 5, 7, and 14. After 14 days of culture, the HA, HS, and CS in the hydrogel were digested at 37° C. for 24 hours with a release buffer containing 10 U hyaluronidase, 100 mU heparinase II, and 20 mU chondroitin sulfate ABC. The collected release buffer was quantified using an ELISA kit of growth factors.

As may be seen from FIG. 6A, the portion of the hybrid hydrogels of example 1 and comparative example 2 rapidly degraded at the initial stage should be an uncrosslinked hydrogel precursor. Thereafter, the hybrid hydrogels of example 1 and comparative example 2 continued to be degraded and were completely degraded after about five weeks. As may be seen from FIG. 6B, since the hybrid nanoparticles mCSPCN of the hybrid hydrogel of example 1 were mixed with HA-ALD before crosslinking, the forming of the imine bond (between the primary amine on the peptide of the hybrid nanoparticles mCSPCN and the aldehyde group on the HA-ALD) resulted in a slower release of the hybrid nanoparticles mCSPCN of the hybrid hydrogel of example 1, and the hybrid nanoparticles mCSPCN accumulated about 80% of the release amount after 5 weeks. In contrast, since there was no bond between the hybrid nanoparticles CSPCN of the hybrid hydrogel of comparative example 2 and the HA-ALD, the hybrid nanoparticles CSPCN of the hybrid hydrogel of comparative example 2 were rapidly released significantly on day 1 (about 40%), and the hybrid nanoparticles CSPCN were only released for 14 days. FIG. 6C shows that, the slopes of the fitted trend lines of the hybrid hydrogel of example 1 and the hybrid hydrogel of comparative example 2 were respectively 0.82 and 2.32, indicating the release of the hybrid nanoparticles mCSPCN of the hybrid hydrogel of example 1 and the degradation of the hybrid hydrogel are consistent (slope≤1), which is not caused by the rapid diffusion of the hybrid hydrogel (slope>1).

FIG. 7A is fluorescence analysis image for a cytotoxicity test of the hybrid hydrogels of example 1 and comparative example 1 of the invention. The upper row is the cytotoxicity test result for day 1 of the hybrid hydrogel, and the lower row is the cytotoxicity test result for day 3 of the hybrid hydrogel. In this test, the cells tested were selected from rat neural stem cells (semi adhesive HCN-A94-2). As may be seen from FIG. 7A, living cells occupy a dominant position, and only a small number of dead cells are observed.

FIG. 7B is a diagram of the cytotoxicity test analysis of the hybrid hydrogel of example 1 of the invention. Negative control (group) represents cells culture in tissue culture polystyrene. Positive control (group) represents the complete poisoning of cell by breaking cell membranes using Triton X-100. As may be seen from FIG. 7B, the cytotoxicity of the hybrid hydrogel of example 1 is not significantly different from that of the negative control (group).

Experiment 3

Hereinafter, the characteristic test of in vitro controlled signaling regulation of the hybrid hydrogel of the invention in neural stem cells is described in detail with reference to FIG. 8A to FIG. 10B.

Figure 8D:
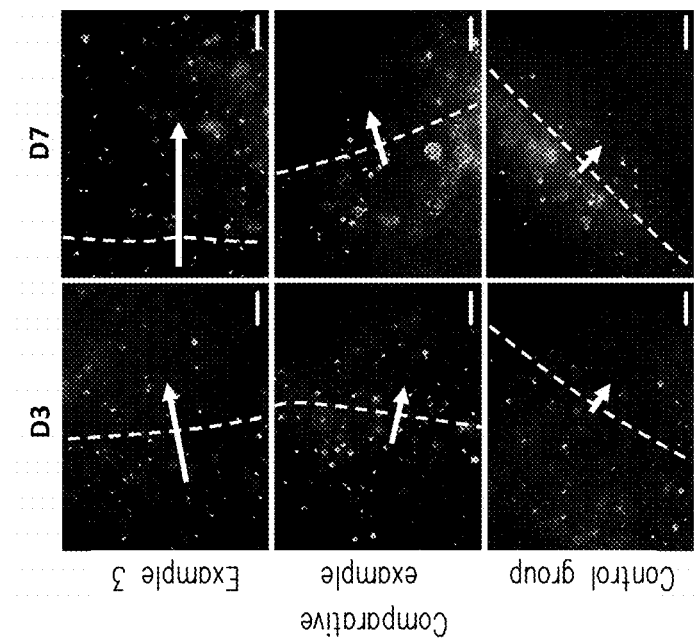
FIG. 8D is a fluorescent analysis image of the combination of the hybrid hydrogel and Matrigel for the cell migration assay of example 3 of the invention.
Figure 8A:
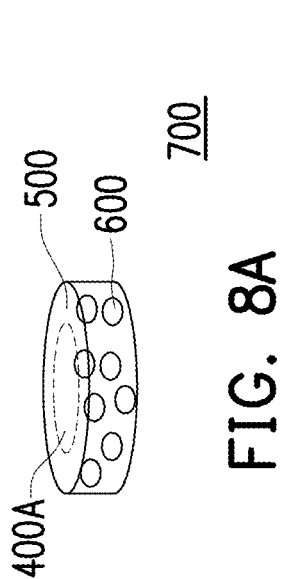
FIG. 8A is a schematic structural view showing a combination of a hybrid hydrogel and Matrigel for a cell migration assay according to some embodiments of the invention.

FIG. 8A is a schematic structural view showing a combination of a hybrid hydrogel and Matrigel for a cell migration assay according to some embodiments of the invention. In FIG. 8A, the chemotactic migration of the neural stem cells in the hybrid hydrogel was tested using a cylindrical hydrogel 700 as shown in FIG. 8A, wherein the hybrid hydrogel 400A is located at the core of the cylindrical hydrogel 700, and the Matrigel 500 containing neural stem cells 600 is located at the outer ring of the cylindrical hydrogel 700.

Figure 8C:
FIG. 8C is a partially enlarged fluorescence analysis image of FIG. 8B.
Figure 8B:
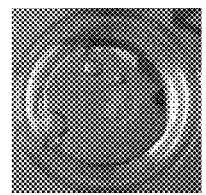
FIG. 8B is a microscopic observation image of the combination of the hybrid hydrogel and Matrigel shown in FIG. 8A.
Figure 8E:
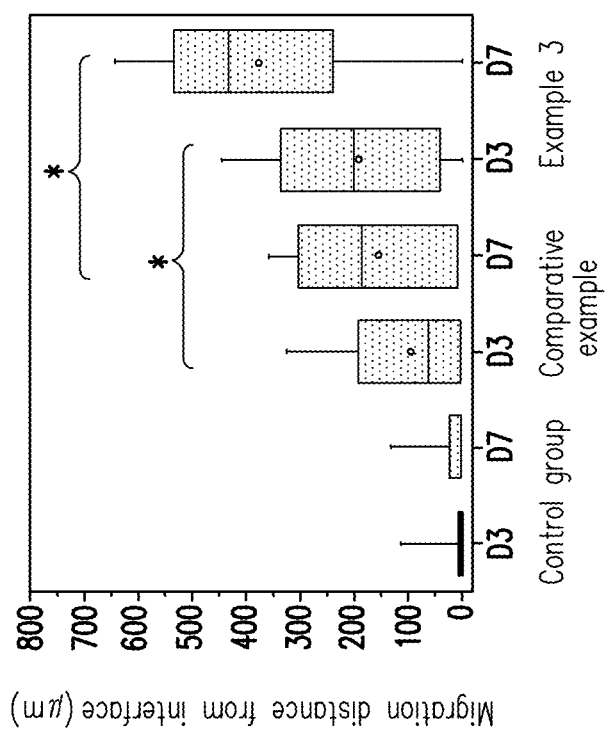
FIG. 8E is a diagram showing the cell migration assay analysis of the combination of the hybrid hydrogel and Matrigel of example 3 of the invention.

FIG. 8B is a microscopic observation image of the combination of the hybrid hydrogel and Matrigel shown in FIG. 8A. FIG. 8C is a partially enlarged fluorescence analysis image of FIG. 8B. FIG. 8D is a fluorescent analysis image of the combination of the hybrid hydrogel and Matrigel for the cell migration assay of example 3 of the invention. FIG. 8E is a diagram showing the cell migration assay analysis of the combination of the hybrid hydrogel and Matrigel of example 3 of the invention. In FIG. 8D, the control group indicates the core of the hydrogel 700 is formed by the hydrogel material 300, i.e., the core consists solely of the hydrogel material 300, and the comparative group indicates the core of the cylindrical hydrogel 700 is formed by the hydrogel material 300 additionally mixing with SDF-1α, but SDF-1α is free SDF-1α. The left column is the fluorescence analysis image on day 3, and the right column is the fluorescence analysis image on day 7. The dashed line represents the interface between the core and the outer ring, the arrow represents the direction of migration of the neural stem cells, and the length of the arrow represents the overall migration direction of the neural stem cells. As may be seen from FIG. 8D and FIG. 8E, the neural stem cells of example 3 and the comparative group both migrated across the interface toward the core of the cylindrical hydrogel 700 on day 3, wherein the distance of migration of the neural stem cells of example 3 was about 200 μm on average, and the distance of migration of the neural stem cells of the comparative group was about 100 μm on average.

Figure 9B:
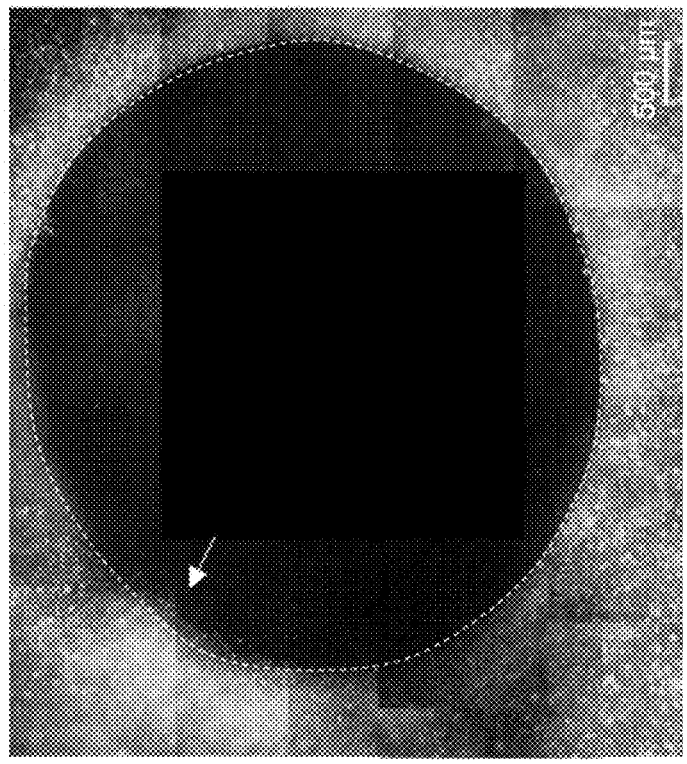
FIG. 9A and FIG. 9B are respectively diagrams of cell migration assay analysis of the combinations of the hybrid hydrogel and Matrigel of example 4 and example 6 of the invention.
Figure 9A:
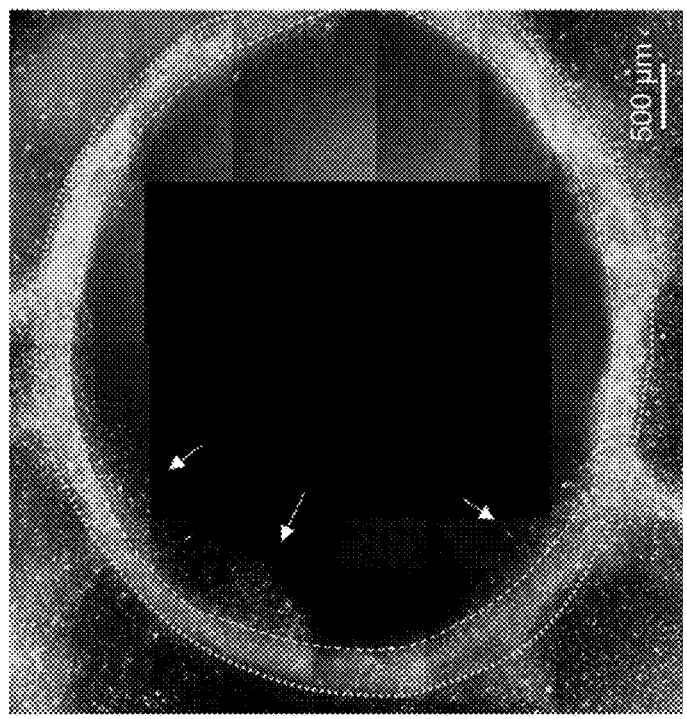

FIG. 9A and FIG. 9B are respectively diagrams of cell migration assay analysis of the combinations of the hybrid hydrogels and Matrigel of example 4 and example 6 of the invention. The outer circle dashed line represents the interface between the starting core and the outer ring, the inner circle dashed line represents the interface of cell migration after 3 days, and the arrow represents the migration of the neural stem cells. FIG. 9A and FIG. 9B show that, the hybrid hydrogel non-mHSPCN of example 6 is not enzyme-sensitive to matrix metalloproteinase (MMP), and thus does not change the movement of the surrounding neural stem cells.

FIG. 10A is a microscopic observation image of a cell proliferation assay of the combinations of the hybrid hydrogels and Matrigel of example 2 and example 4 of the invention. FIG. 10B is a diagram of the analysis of the cell proliferation assay of the combinations the hybrid hydrogels and Matrigel of example 2 and example 4 of the invention. In FIG. 10A, the results of cell proliferation observation on day 1, day 3, and day 7 are represented from top to bottom, respectively. As may be seen from FIG. 10A, neurosphere-like neural stem cell aggregates (about 50 µm to 100 µm in diameter) were observed on day 3 in the hybrid hydrogel of example 4, and the neural stem cell aggregates gradually got bigger until day 7. The neural stem cells in the hybrid hydrogel of example 2 were still evenly dispersed on day 3. As may be seen from FIG. 10B, the DNA content in the hybrid hydrogel of example 4 is significantly higher than the DNA content in the hybrid hydrogel of example 2.

Experiment 4

Hereinafter, the treatment effect of the hybrid hydrogel of the invention on brain damage and the test of endogenous cell regeneration are described in detail with reference to FIG. 11A to FIG. 14B.

Figure 11A:
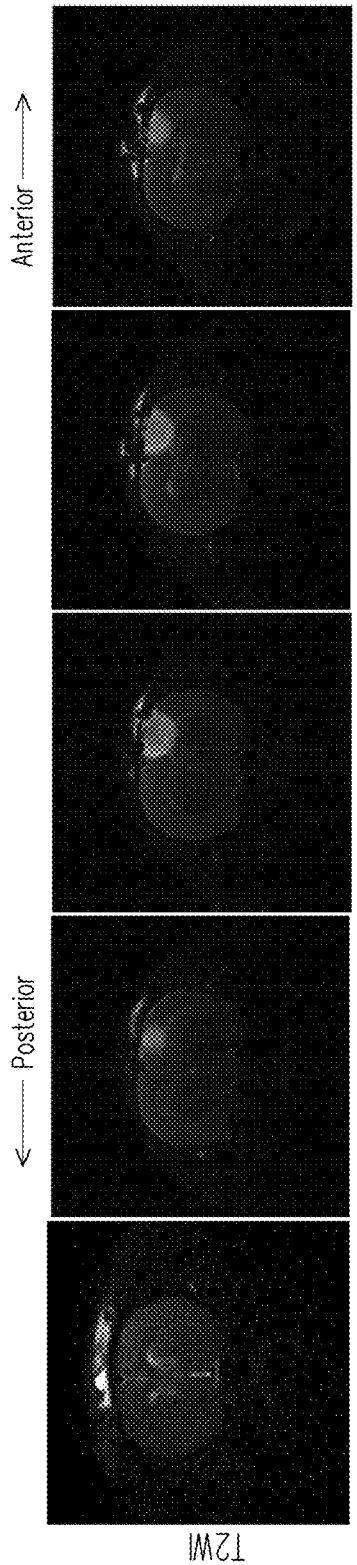
FIG. 11A and FIG. 11B are NMRIs of a rat brain after damage.
Figure 11B:
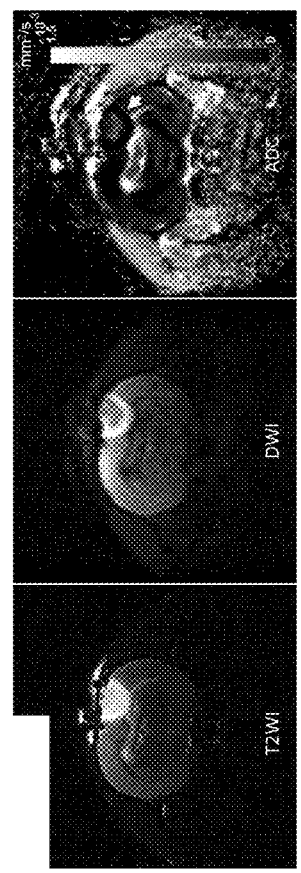

FIG. 11A and FIG. 11B are NMRIs of a rat brain after damage. A rat model of photothrombotic ischemia (PTI) was used as a treatment effect test of the hybrid hydrogel of the invention for brain damage. In FIG. 11B, the left side is a T2-weighted image (T2WI), the middle is a diffusion-weighted image (DWI), and the right side is an apparent diffusion coefficient (ADC) map. In T2WI, the more liquid is filled, the brighter the area displayed. In DWI, the more difficult the liquid flows, the brighter the area displayed. As may be seen from FIG. 11A and FIG. 11B, the right hemisphere cerebral cortex shows a relatively even high signal from the surface of the cortex to the carcass at the laser irradiation site, and the average volume of the high signal region is 51.9±4.2 mm$^3$. The signal in the diffusion-weighted image is increased and the signal in the apparent diffusion coefficient map is reduced by colocalization with the T2 high signal region.

Figure 11D:
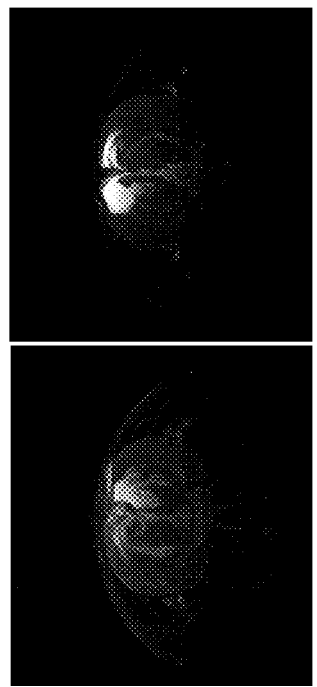
FIG. 11D is an NMRI for treating brain damage in rats using the hybrid hydrogel of example 5 and the control group of the invention.
Figure 11C:
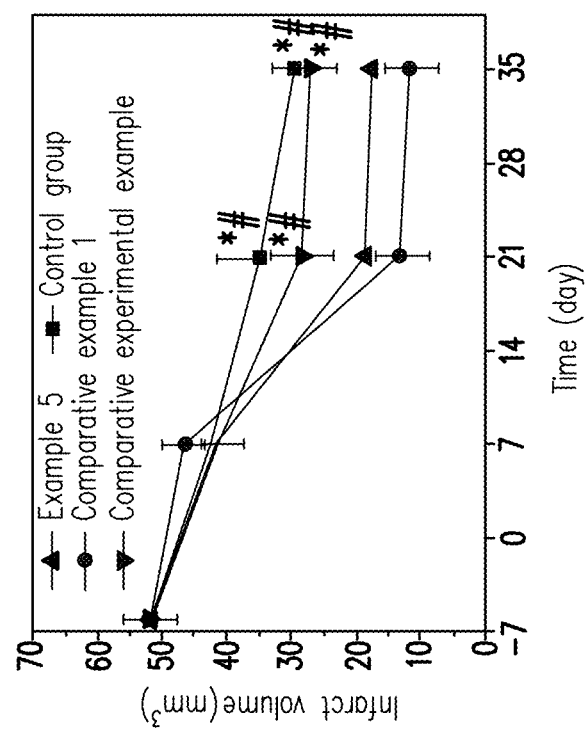
FIG. 11C is a diagram of the result analysis for treating brain damage in rats using the hybrid hydrogel of example 5, the hydrogel of comparative example 1, the hybrid nanoparticles of the comparative experimental example, and the control group of the invention shown according to an NMRI image.

FIG. 11C is a diagram of the result analysis for treating brain damage in rats using the hybrid hydrogel of example 5, the hydrogel of comparative example 1, the hybrid nanoparticles of the comparative experimental example, and the control group of the invention shown according to an NMRI image. FIG. 11D is an NMRI of the hybrid hydrogel of example 5 and the control group of the invention for treating brain damage in rats. The figures of FIG. 11D are mirror images of the original photo pictures, and the left and right figures of FIG. 11D respectively represent the nuclear magnetic resonance images of the hybrid hydrogel of example 5 and the control group on day 35. The control group represents only PBS was injected into the damaged portion of the rat brain. As may be seen from FIG. 11C and FIG. 11D, the infarct volumes of the injection into the damaged portion of the rat brain using the hybrid hydrogel of example 5 and the hydrogel of comparative example 1 are significantly reduced on day 21 compared to the comparative experimental example and the control group. The infarct volume of the injection into the damaged portion of the rat brain using the hybrid hydrogel of example 5 is significantly reduced on day 35 compared to the control group.

Figure 12:
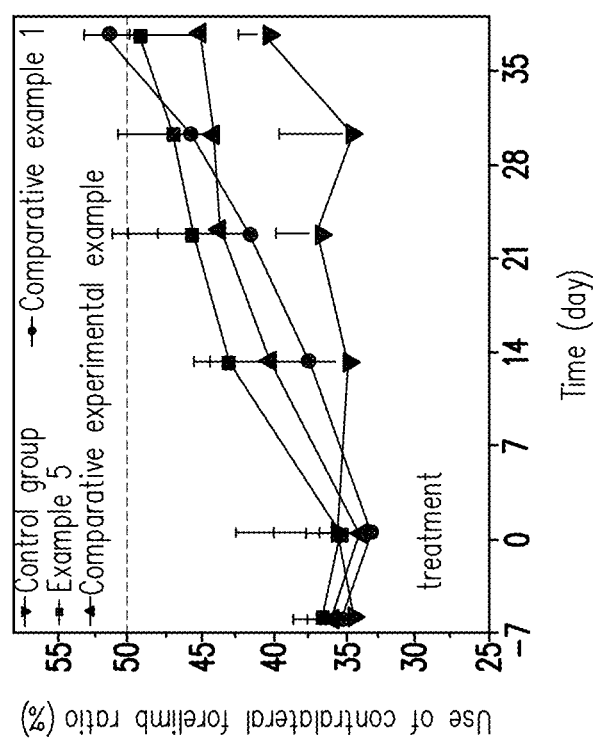
FIG. 12 is a diagram of the result analysis for treating brain damage in rats using the hybrid hydrogel of example 5, the hydrogel of comparative example 1, the hybrid nanoparticles of the comparative experimental example, and the control group of the invention shown according to the behavior of the rats.

FIG. 12 is a diagram of the result analysis for treating brain damage in rats using the hybrid hydrogel of example 5, the hydrogel of comparative example 1, the hybrid nanoparticles of the comparative experimental example, and the control group of the invention shown according to the behavior of the rats. In FIG. 12, the use contralateral forelimb ratio was calculated by the following formula 1:

$$\text{Use contralateral forelimb ratio}(\%) = \frac{\frac{\text{movement of left limb} + \text{movement of both limbs}}{2}}{\text{total movement(left limb} + \text{right limb} + \text{both limbs)}} \times 100\%$$

As may be seen from FIG. 12, after the hybrid hydrogel of example 5 and the hydrogel of comparative example 1 were injected into the damaged portion of the rat brain, the ratio of the contralateral forelimb for the rats was significantly increased after day 28 compared to the comparative experimental example and the control group.

Figure 13B:
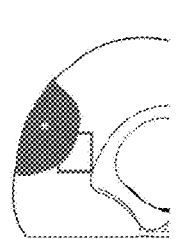
Figure 13B:
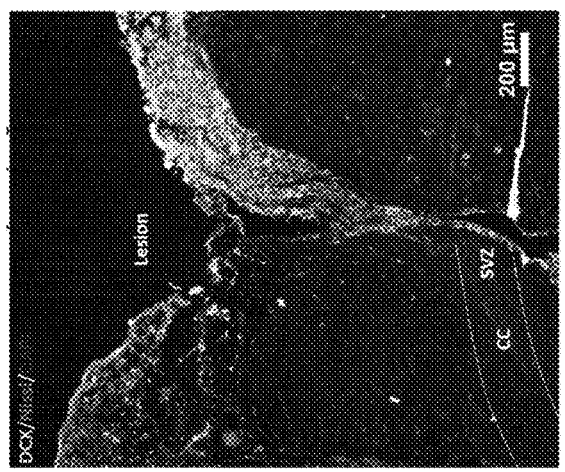
Figure 13A:
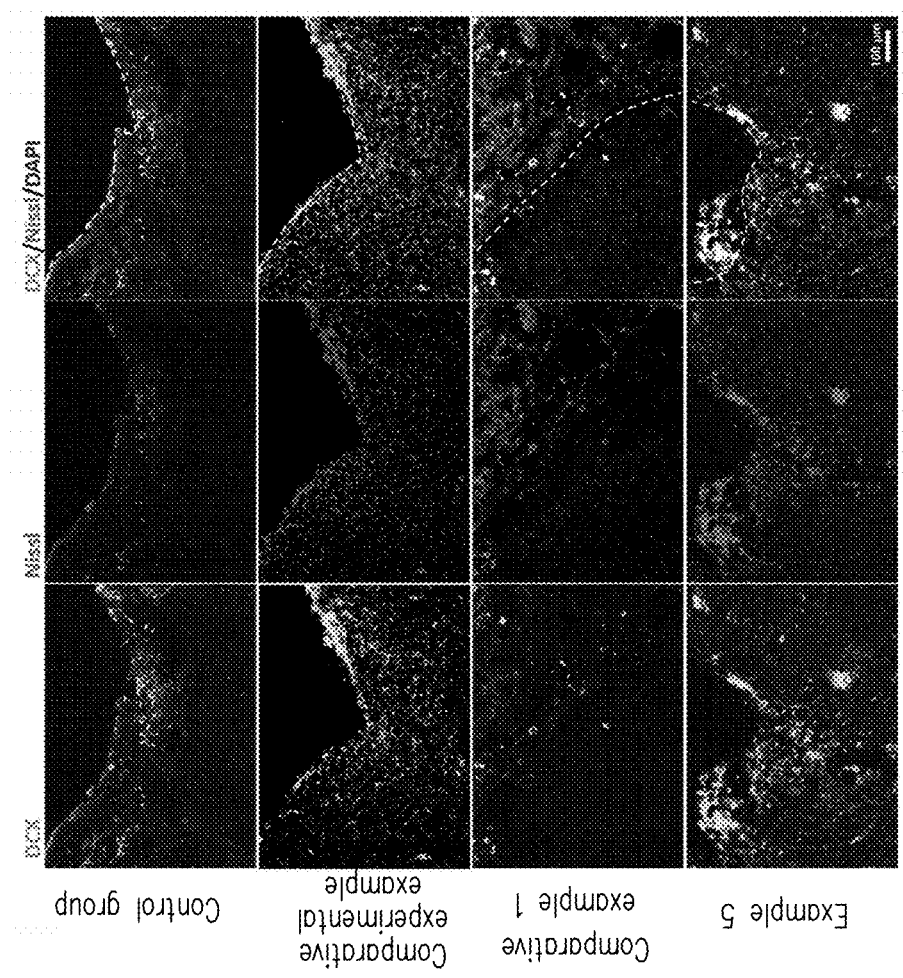

FIG. 13A to FIG. 13C are immunofluorescence staining images of brain tissue sections for treating brain damage in rats using the hybrid hydrogel of example 5, the hydrogel of comparative example 1, the hybrid nanoparticles of the comparative experimental example, and the control group of the invention. FIG. 13D and FIG. 13E are diagrams of the result analysis for treating brain damage in rats using the hybrid hydrogel of example 5, the hydrogel of comparative example 1, the hybrid nanoparticles of the comparative experimental example, and the control group of the invention shown according to immunofluorescence staining images of brain tissue sections. The DCX may be used as a marker to identify migratory neural precursor cells, and Ki67 and Nestin may be used as proliferation markers for calculating neural precursor cells. FIG. 13A to FIG. 13E show that, after the injection of the hybrid hydrogel of example 5 to the damaged portion of the rat brain, the neural precursor cells significantly migrated around the infarct chamber after day 21 of treatment, and many nerve precursor cells proliferated around the infarction tissue.

Figure 14A:
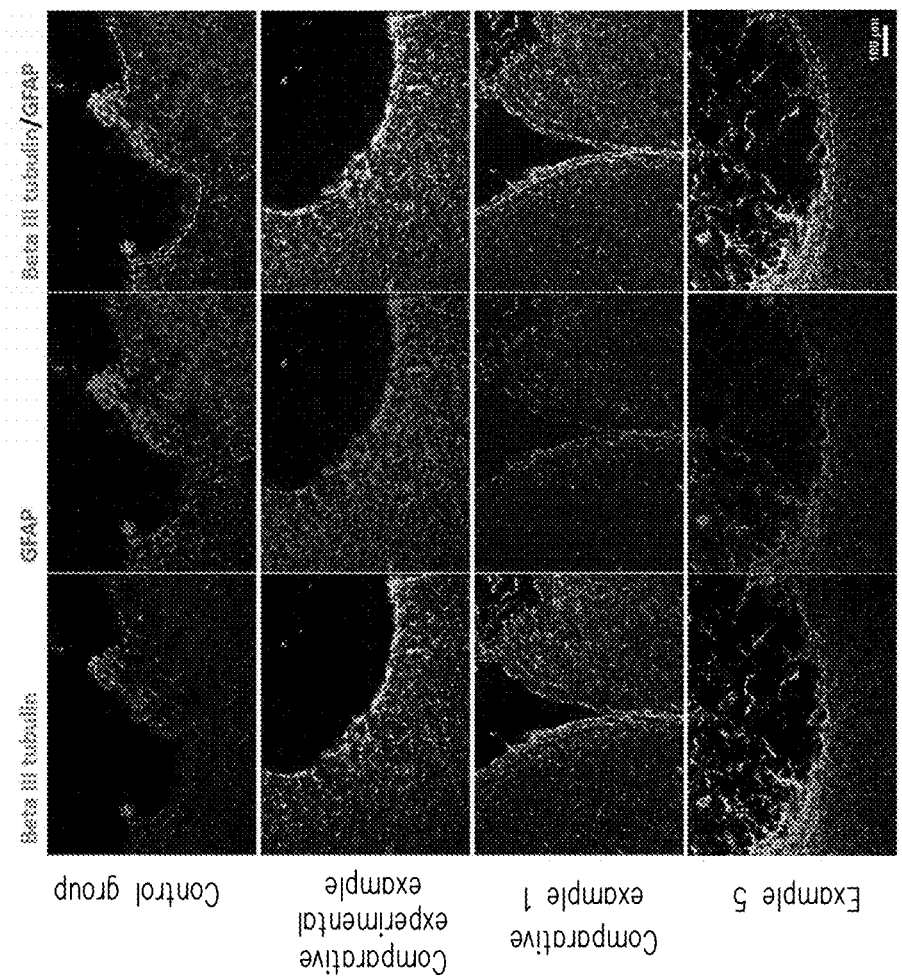
FIG. 14A is an immunofluorescence staining image near a brain tissue infarction section for treating brain damage in rats using the hybrid hydrogel of example 5, the hydrogel of comparative example 1, the hybrid nanoparticles of the comparative experimental example, and the control group of the invention.
Figure 14B:
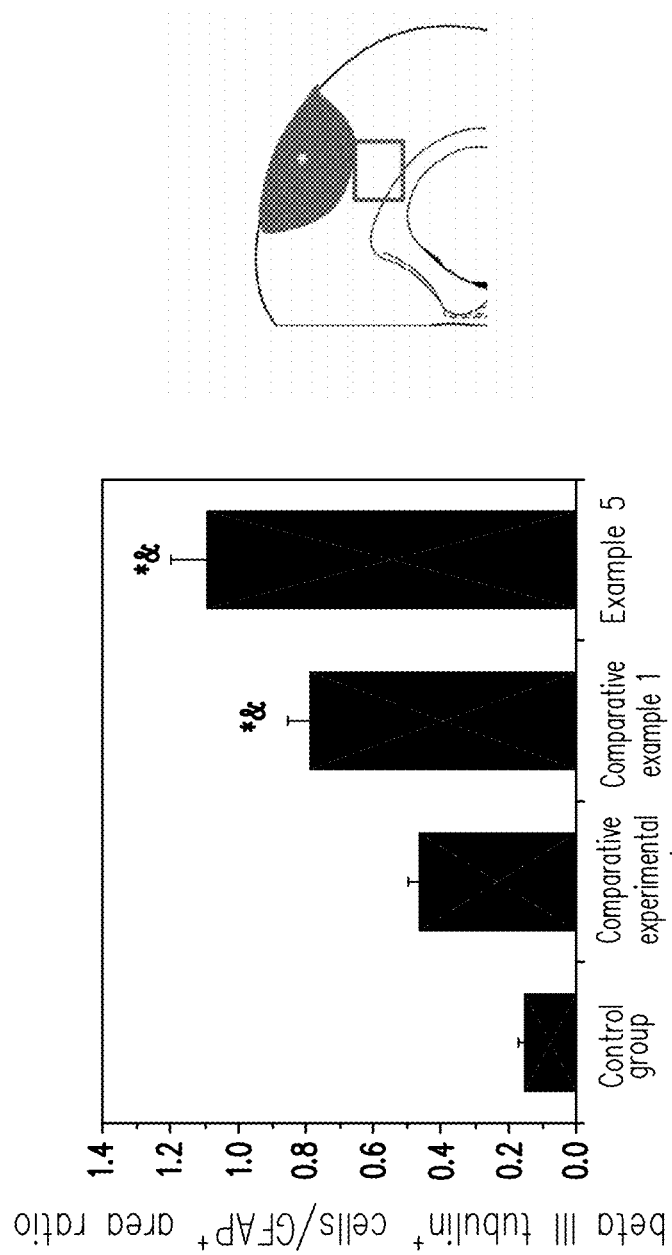
FIG. 14B is a diagram of the result analysis for treating brain damage in rats using the hybrid hydrogel of example 5, the hydrogel of comparative example 1, the hybrid nanoparticles of the comparative experimental example, and the control group of the invention shown according to an immunofluorescence staining image near a brain tissue infarction section.
Figure 14C:
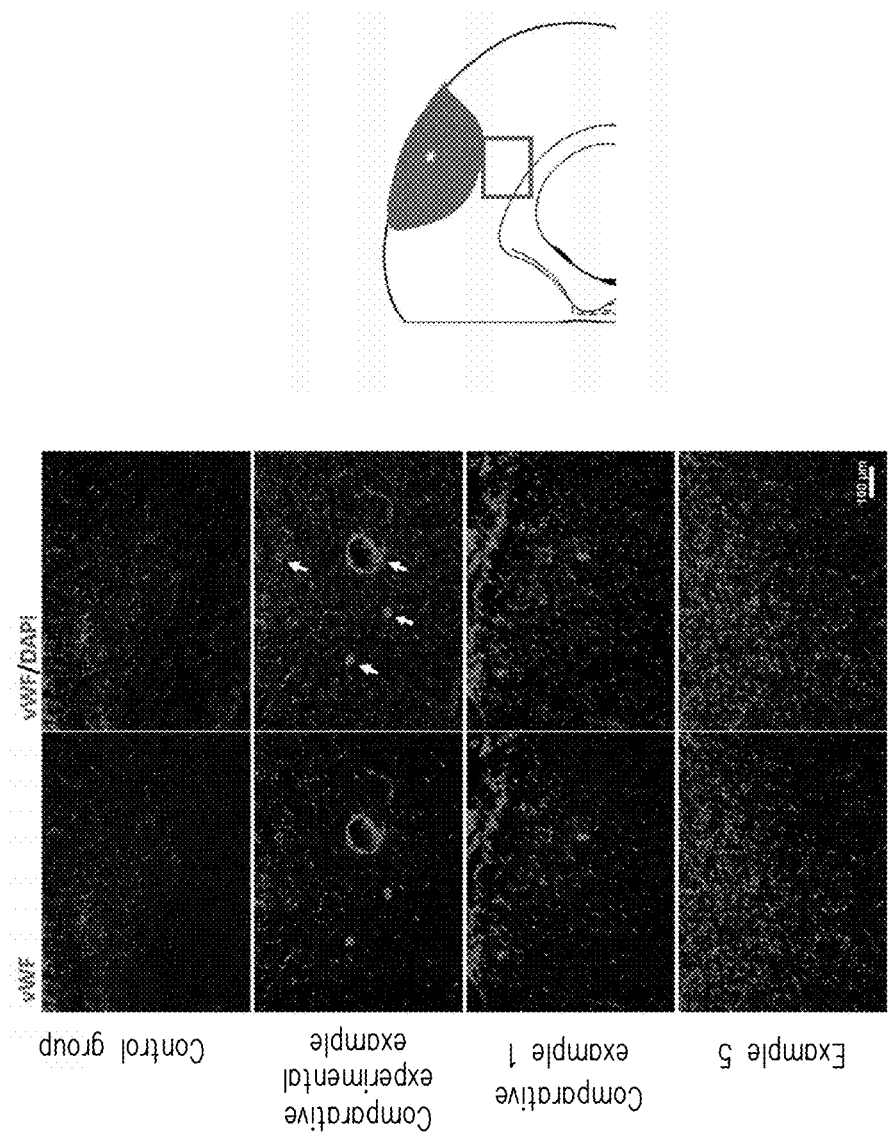
FIG. 14C is an immunofluorescence staining image of a brain tissue infarction surrounding section for treating brain damage in rats using the hybrid hydrogel of example 5, the hydrogel of comparative example 1, the hybrid nanoparticles of the comparative experimental example, and the control group of the invention.

FIG. 14A is an immunofluorescence staining image for treating brain damage in rats near a brain tissue infarction section using the hybrid hydrogel of example 5, the hydrogel of comparative example 1, the hybrid nanoparticles of the comparative experimental example, and the control group of the invention. FIG. 14B is a diagram of the result analysis for treating brain damage in rats using the hybrid hydrogel of example 5, the hydrogel of comparative example 1, the hybrid nanoparticles of the comparative experimental example, and the control group of the invention shown according to an immunofluorescence staining image near a brain tissue infarction section. FIG. 14C is an immunofluorescence staining image of a brain tissue infarction surrounding section for treating brain damage in rats using the hybrid hydrogel of example 5, the hydrogel of comparative example 1, the hybrid nanoparticles of the comparative experimental example, and the control group of the invention. In order to analyze the neural phenotype during regeneration, β-III butulin and glial fibrillary acidic protein (GFAP) may be used as markers for the assessment of the formation of immature neurons and astrogliosis. As may be seen from FIG. 14A to FIG. 14C, injection of the hybrid hydrogel of example 5 and the hydrogel of comparative example 1 to the damaged portion of the rat brain reduced astrogliosis and promoted the formation of immature neurons.

Based on the above, the hybrid hydrogel of the invention includes a hydrogel material and hybrid nanoparticles, and a suitable combination of hydrogel material and hybrid nanoparticles may be selected according to requirements to achieve a better treatment effect. In therapeutic applications of brain damage, the hydrogel material may mimic the microenvironment of brain tissue and achieve the effect of structural support. The negative-charged polysaccharide in the hybrid nanoparticles may protect and carry different growth factors, and the load efficiency of the growth factors is high. The peptides conjugated to the hydrogel material and the hybrid nanoparticles may regulate the release rate of the hybrid nanoparticles, thereby controlling the release of the growth factors carried by the hybrid nanoparticles to achieve better treatment effects.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:
1. A hybrid hydrogel, comprising:
a hydrogel material;
a plurality of first hybrid nanoparticles conjugated to the hydrogel material by a matrix metalloproteinase (MMP)-sensitive bond, wherein each of the first hybrid nanoparticles comprises:
a first positive-charged polysaccharide located at an inner core of the first hybrid nanoparticles; and
a first negative-charged polysaccharide located at an outer shell of the first hybrid nanoparticles and carrying a plurality of first growth factors, wherein the first negative-charged polysaccharide and the first positive-charged polysaccharide are electrostatically attracted to form the first hybrid nanoparticles, wherein the first negative-charged polysaccharide is conjugated to a MMP-sensitive peptide, and the MMP-sensitive bond is formed by reacting the MMP-sensitive peptide with the hydrogel material, wherein the first negative-charged polysaccharide comprises heparin sulfate and the first growth factors comprise stromal cell-derived factors-1 alpha (SDF-1 α); and
a plurality of second hybrid nanoparticles conjugated to the hydrogel material by a non-MMP-sensitive bond, wherein each of the second hybrid nanoparticles comprises:
a second positive-charged polysaccharide located at an inner core of the second hybrid nanoparticles; and
a second negative-charged polysaccharide located at an outer shell of the second hybrid nanoparticles and carrying a plurality of second growth factors, wherein the second negative-charged polysaccharide and the second positive-charged polysaccharide are electrostatically attracted to form the second hybrid nanoparticles, wherein the second negative-charged polysaccharide is conjugated to a non-MMP-sensitive peptide, and the non-MMP-sensitive bond is formed by reacting the non-MMP-sensitive peptide with the hydrogel material, wherein the second negative-charged polysaccharide comprises chondroitin sulfate and the second growth factors comprise basic fibroblast growth factors (bFGF).

2. The hybrid hydrogel of claim 1, wherein the first negative-charged polysaccharide, and the second negative-charged polysaccharide further comprise proteoglycan.

3. The hybrid hydrogel of claim 1, wherein the first positive-charged polysaccharide and the second positive-charged polysaccharide comprise chitosan.

4. The hybrid hydrogel of claim 1, wherein the first negative-charged polysaccharide and the second negative-charged polysaccharide further comprise dermatan sulfate, keratin sulfate, or a combination thereof.

5. The hybrid hydrogel of claim 1, wherein the first growth factors and the second growth factors further comprise platelet-derived growth factors (PDGF), vascular endothelial growth factors (VEGF), hepatocyte growth factors (HGF), bone morphogenetic proteins (BMP), or a combination thereof.

6. The hybrid hydrogel of claim 1, wherein the first growth factors and the second growth factors are the same or different growth factors.

7. The hybrid hydrogel of claim 1, wherein the hydrogel material comprises a biodegradable hydrogel material.

8. The hybrid hydrogel of claim 1, wherein the hydrogel material comprises glycosaminoglycan, polysaccharide, protein, or a combination thereof.

9. The hybrid hydrogel of claim 1, wherein the hydrogel material comprises hyaluronic acid, alginic acid, chitosan, collagen, or a combination thereof.

10. The hybrid hydrogel of claim 1, wherein particle sizes of the plurality of first hybrid nanoparticles and the plurality of second hybrid nanoparticles are between 100 nm and 500 nm.

11. The hybrid hydrogel of claim 1, wherein a molecular weight of the first positive-charged polysaccharide is smaller than a molecular weight of the first negative-charged polysaccharide, and a molecular weight of the second positive-charged polysaccharide is smaller than a molecular weight of the second negative-charged polysaccharide.

12. The hybrid hydrogel of claim 1, wherein a storage modulus of the hybrid hydrogel after gelation is between 100 Pa and 1000 Pa.

13. A method for fabricating a hybrid hydrogel, comprising:
providing a hydrogel material;
forming a plurality of first hybrid nanoparticles conjugated to the hydrogel material by a matrix metalloproteinase (MMP)-sensitive bond, wherein each of the first hybrid nanoparticles comprises:
a first positive-charged polysaccharide located at an inner core of the first hybrid nanoparticles; and
a first negative-charged polysaccharide located at an outer shell of the first hybrid nanoparticles and carrying a plurality of first growth factors, wherein the first negative-charged polysaccharide and the first positive-charged polysaccharide are electrostatically attracted to form the first hybrid nanoparticles, wherein the first negative-charged polysaccharide is conjugated to a MMP-sensitive peptide, and the MMP-sensitive bond is formed by reacting the MMP-sensitive peptide with the hydrogel material, wherein the first negative-charged polysaccharide comprises heparin sulfate and the first growth factors comprise stromal cell-derived factors-1 alpha (SDF-1 α); and
forming a plurality of second hybrid nanoparticles conjugated to the hydrogel material by a non-MMP-sensitive bond, wherein each of the second hybrid nanoparticles comprises:
a second positive-charged polysaccharide located at an inner core of the second hybrid nanoparticles; and a second negative-charged polysaccharide located at an outer shell of the second hybrid nanoparticles and carrying a plurality of second growth factors, wherein the second negative-charged polysaccharide and the second positive-charged polysaccharide are electrostatically attracted to form the second hybrid nanoparticles, wherein the second negative-charged polysaccharide conjugated to a non-MMP-sensitive peptide and the non-MMP-sensitive bond is formed by reacting the non-MMP-sensitive peptide with the hydrogel material, wherein the second negative-charged polysaccharide comprises chondroitin sulfate and the second growth factors comprise basic fibroblast growth factors (bFGF).

14. The method of fabricating the hybrid hydrogel of claim 13, wherein the step of forming the MMP-sensitive bond or the non-MMP-sensitive bond comprises:
   modifying the hydrogel material to have an aldehyde group; and
   forming the MMP-sensitive bond or non-MMP-sensitive bond by reacting an amino group of the MMP-sensitive peptide or the non-MMP-sensitive peptide with the aldehyde group of the hydrogel material.

15. The method of fabricating the hybrid hydrogel of claim 13, wherein the first growth factors and the second growth factors are the same or different growth factors.

* * * * *